United States Patent [19]

Ha et al.

[11] Patent Number: 5,997,887
[45] Date of Patent: Dec. 7, 1999

[54] SKIN CARE COMPOSITIONS AND METHOD OF IMPROVING SKIN APPEARANCE

[75] Inventors: Robert Bao Kim Ha, Milford; Timothy John Fowler, Cincinnati, both of Ohio

[73] Assignee: The Procter & Gamble Company, Cincinnati, Ohio

[21] Appl. No.: 08/966,840

[22] Filed: Nov. 10, 1997

[51] Int. Cl.[6] .................................................. A61K 7/48
[52] U.S. Cl. .................... 424/401; 514/937; 514/938; 514/944; 514/844; 514/845; 514/846; 514/847; 424/69; 424/70.1
[58] Field of Search ................... 424/401, 69, 70.1; 514/937, 938, 944, 844, 845, 846, 847

[56] References Cited

U.S. PATENT DOCUMENTS

| | | | |
|---|---|---|---|
| 4,820,518 | 4/1989 | Murphy et al. | 424/401 |
| 5,068,056 | 11/1991 | Robb | 252/313.1 |
| 5,122,418 | 6/1992 | Nakane et al. | 424/401 |
| 5,223,559 | 6/1993 | Arraudeau et al. | 524/47 |
| 5,443,759 | 8/1995 | Dahms | 252/302 |
| 5,476,660 | 12/1995 | Somasudaran et al. | 424/401 |
| 5,516,457 | 5/1996 | Dahms | 252/302 |
| 5,585,104 | 12/1996 | Ha et al. | 424/401 |

FOREIGN PATENT DOCUMENTS

| | | | |
|---|---|---|---|
| 504066A1 | 9/1992 | European Pat. Off. | |
| 62-209011 | 9/1987 | Japan | A61K 7/02 |
| 2 280 605 | 2/1995 | United Kingdom. | |
| 2 291 804 | 2/1996 | United Kingdom. | |
| 2 300 629 | 11/1996 | United Kingdom. | |
| WO 93/18852 | 9/1993 | WIPO | B01J 13/00 |
| WO 93/2342 | 11/1993 | WIPO. | |
| WO 94/06406A1 | 3/1994 | WIPO | A61K 7/48 |
| WO 94/15580 | 7/1994 | WIPO | A61K 7/42 |
| WO 96/19180 | 6/1996 | WIPO | A61K 7/100 |

OTHER PUBLICATIONS

KOBO Products, Inc., Product List Technical Data (4 pgs).
KOBO Products, Inc., New Dispersions (10 pgs.).
Emmert, "Quantification of the Soft–Focus Effect", *Cosmetics & Toiletries*, vol. III, pp. 57–61, 1996.
Ahlnas, Zeta Potential: An Important Aspect in Formulating, Kemira Technical Seminar, Oct. 3, 1994.
Tambe et al., "Factors Controlling the Stability of Colloid–Stabilized Emulsions", *J. of Colloid and Interface Sci.*, vol. 157, pp. 244–253 (1993).
Lee et al., "Preparation of Ultrafine $Fe_3O_4$ Particles by Precipitation in the Presence of PVA at High pH", *J. of Colloid and Interface Sci.*, vol. 177, pp. 490–494 (1996).

*Primary Examiner*—Jyothsna Venkat
*Attorney, Agent, or Firm*—George W. Allen; Armina E. Matthews

[57] ABSTRACT

Disclosed are topical compositions which provide good coverage of skin imperfections, e.g., pores and uneven skin tone, while retaining a natural skin appearance. The compositions contain a charged particulate material dispersed throughout a thickened, hydrophilic carrier. The charged particulate material allows the compositions to have a Coverage Efficiency Ratio of greater than about 20.

18 Claims, No Drawings

SKIN CARE COMPOSITIONS AND METHOD OF IMPROVING SKIN APPEARANCE

TECHNICAL FIELD

The present invention relates to the field of topical compositions, e.g., skin care compositions, suitable for improving the appearance or other condition of skin. More particularly, the invention relates to topical skin care compositions which provide good coverage of skin imperfections, e.g., pores and uneven skin tone, while permitting skin to retain a natural appearance.

BACKGROUND OF THE INVENTION

Consumers have used cosmetic products to care for their skin since the dawn of civilization. These products have ranged from simple, commonly-available materials such as honey and plant extracts to, in recent years, hi-tech synthetic ingredients in a wide variety and array of product forms.

Numerous compounds have been described in the art as being useful for regulating skin condition, including regulating fine lines, wrinkles and other forms of uneven or rough surface texture associated with aged or photodamaged skin. However, many materials require multiple applications over an extended period to provide such appearance benefits. It would be advantageous to provide a topical composition which provides a more immediate improvement in the appearance of fine lines, wrinkles, pores and other forms of undesirable skin surface texture.

One approach has been to incorporate particulate materials, such as $TiO_2$, into skin care compositions. For example, emulsions may contain TiO2 as an opacifying agent to provide a white appearance to the emulsion. Commercial sunscreening compositions may employ such particulates to impart a sunscreening effect. Several publications have also disclosed the use of $TiO_2$ in skin care compositions. See, e.g., U.S. Pat. No. 5,223,559 and patent application Nos. DE 245815, WO 94/09756 and JP 08188723. In addition, R. Emmert has stated the desire to use optical means to formulate products that give the consumer an immediate, visual improvement (Dr. Ralf Emmert, *Quantification of the Soft-Focus Effect*, Cosmetics & Toiletries, Vol. III, July 1996, pp. 57–61). Emmert discloses that one can mechanically fill in skin lines with a reflective substance such as $TiO_2$. However, Emmert teaches that such reflective materials result in an undesirable mask-like appearance, and that one should therefore use a material that diffuses light yet is sufficiently transparent to avoid the mask-like appearance.

Known topical compositions containing reflective materials such as $TiO_2$, generally either do not provide coverage sufficient to reduce the appearance of skin imperfections, or tend to result in unacceptable skin whitening or other unnatural appearance when applied to the skin. It has also now been found that materials which primarily diffuse light, rather than reflect light, do not provide good coverage of skin imperfections when used in amounts which are aesthetically acceptable to consumers. More particularly, when used at relatively high concentrations to provide coverage, these materials suffer from unacceptable skin whitening.

Additionally, reflective particulate materials, such as $TiO_2$, tend to feel dry and add to the negative perception that the composition is not being absorbed into the skin and/or that the composition is not providing a skin conditioning benefit. As a result, relatively high concentrations contribute to amplify these negative qualities. It has also been found that reflective particulate materials tend to agglomerate, e.g., cluster together. When these materials agglomerate greater amounts of particulate materials are required to provide sufficient coverage, which also adds to the negative perceptions. Thus, it would be desirable to realize aesthetically acceptable degrees of skin coverage even though relatively low concentrations of $TiO_2$ are used.

In addition, it is desirable for cosmetic compositions to have good aesthetics during application onto the skin and while on the skin. Good aesthetics means that the composition (i) is light and nongreasy, (ii) has a smooth, silky feel upon the skin, (iii) spreads easily, and (iv) absorbs quickly. These desirable aesthetics are often achieved by incorporating thickening agents into a composition. However, it is known that particulate materials, such as metal oxides, are often not compatible with many thickening agents, such as carboxylic acid polymers, and skin care actives.

The present invention overcomes the problems discussed hereinbefore (e.g., unacceptable skin whitening, aesthetics, and formulation compatibility issues) by employing charged, surface-treated, reflective particulate materials which are dispersed in a thickened hydrophilic carrier. Surface treated particulates are known in the cosmetic industry, however, their use heretofore has been typically limited to non-aqueous phases and anhydrous-based products such as lipsticks, powders, mascaras, and to heavy, oil-based emulsions. It has been found in the present invention that charged, surface treated reflective particulates (i) are compatible with polymeric thickeners, such as carboxylic acid polymers, (ii) can provide acceptable degrees of skin coverage at relatively low concentrations, and (iii) can be formulated into compositions having excellent aesthetics. Such compositions are especially suitable for providing an immediate visual improvement in skin appearance when topically applied.

In light of the foregoing, it is an object of the present invention to provide topical compositions suitable for imparting an immediate visual improvement in skin appearance.

It is another object of the present invention to provide topical compositions containing a reflective particulate material, e.g., $TiO_2$, which provides desirable coverage of skin imperfections such as pores and uneven skin tone, while maintaining a natural skin appearance (e.g., without unacceptable skin whitening).

It is another object of the present invention to provide topical compositions which provide especially effective skin coverage while using relatively small amounts of reflective particulate material.

It is yet another object of the present invention is to provide such topical compositions which are additionally useful for regulating skin appearance and/or condition, especially regulating textural or tonal discontinuities in skin (e.g., pores and uneven skin color).

Another object of the present invention is to provide topical composition that utilize reflective particulate materials which are compatible with other composition components such as, actives and polymeric thickeners.

It is yet another object of the present invention to provide methods of improving skin appearance and/or condition by topical application of the skin care compositions described herein.

SUMMARY OF THE INVENTION

The present invention relates to skin care compositions which upon topical application to the skin provide immediate visual improvement of skin appearance. Such compositions comprise: (A) from about 1% to about 99.98%, by weight of the composition, of a hydrophilic liquid carrier; (B) from about 0.01% to about 20%, by weight of the composition, of a polymeric thickening agent; and (C) from about 0.01% to about 2%, by weight of the composition, of charged, reflective particulate material having an average primary particle size from about 100 nm to about 300 nm. The charged particulate material is dispersed throughout the thickened hydrophilic liquid carrier. Such compositions provide a Coverage Efficiency Ratio of greater than about 20.

The compositions described herein are preferably in the form of emulsions and contain charged reflective particulate material, such as coated metal oxides. Preferred metal oxides are selected from $TiO_2$, ZnO, and $ZrO_2$, with $TiO_2$ being more preferred. In further preferred embodiments, the present invention relates to compositions which contain one or more compounds selected from the group consisting of emulsifiers, surfactants, structuring agents, skin care actives and combinations thereof.

The present invention also relates to methods of regulating skin condition with the compositions described herein.

DETAILED DESCRIPTION OF THE INVENTION

The compositions of the present invention can comprise, consist essentially of, or consist of, the essential as well as optional ingredients and components described herein. As used herein, "consisting essentially of" means that the composition or component may include additional ingredients, but only if the additional ingredients do not materially alter the basic and novel characteristics of the claimed compositions or methods. All publications cited herein are hereby incorporated by reference in their entirety. All percentages and ratios used herein are by weight of the total composition and all measurements made are at 25° C., unless otherwise designated.

The term "topical application", as used herein, means to apply or spread the compositions of the present invention onto the surface of the skin.

The term "dermatologically-acceptable," as used herein, means that the compositions or components thereof so described are suitable for use in contact with human skin without undue toxicity, incompatibility, instability, allergic response, and the like.

The term "safe and effective amount" as used herein means an amount of a compound, component, or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound medical judgment.

Active and other ingredients useful herein may be categorized or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefore, classifications herein are made for the sake of convenience and are not intended to limit an ingredient to the particularly stated application or applications listed.

The compositions of the invention are useful for topical application and for providing an essentially immediate (i.e., acute) visual improvement in skin appearance following application of the composition to the skin. Without intending to be limited by theory, it is believed that this acute skin appearance improvement results at least in part from therapeutic coverage or masking of skin imperfections by the charged particulate material. The compositions provide the visual benefits without imparting an unacceptable skin appearance such as skin whitening.

More particularly, the compositions of the present invention are useful for regulating skin condition, including regulating visible and/or tactile discontinuities in skin, including but not limited to visible and/or tactile discontinuities in skin texture and/or color, more especially discontinuities associated with skin aging. Such discontinuities may be induced or caused by internal and/or external factors. Extrinsic factors include ultraviolet radiation (e.g., from sun exposure), environmental pollution, wind, heat, low humidity, harsh surfactants, abrasives, and the like. Intrinsic factors include chronological aging and other biochemical changes from within the skin.

Regulating skin condition includes prophylactically and/or therapeutically regulating skin condition. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, such discontinuities. Regulating skin condition involves improving skin appearance and/or feel, e.g., providing a smoother, more even appearance and/or feel. As used herein, regulating skin condition includes regulating signs of aging. "Regulating signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign).

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g., associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

It is to be understood that the present invention is not to be limited to regulation of the above mentioned "signs of skin aging" which arise due to mechanisms associated with skin aging, but is intended to include regulation of such signs irrespective of the mechanism of origin.

The present invention is especially useful for therapeutically regulating visible and/or tactile discontinuities in mammalian skin, including discontinuities in skin texture and color. For example, the apparent diameter of pores decreases, the apparent height of tissue immediately proximate to pore openings approaches that of the interadnexal skin, the skin tone/color becomes more uniform, and/or the length, depth, and/or other dimension of lines and/or wrinkles are decreased.

The compositions of the present invention essentially contain a hydrophilic liquid carrier, a polymeric thickening agent for the hydrophilic liquid carrier, and charged reflective particulate material dispersed throughout the thickened hydrophilic carrier. The compositions herein can also contain a wide variety of optional ingredients. The essential and preferred optional ingredients of the compositions herein, as well as, composition preparation and use are described in detail as follows:

I. Hydrophilic Liquid Carrier

The compositions of the present invention comprise from about 1% to about 99.98%, preferably from about 20% to about 95%, more preferably from about 40% to about 90%, by weight of the composition, of a hydrophilic liquid carrier, e.g., water or other hydrophilic diluent. The hydrophilic liquid carrier can thus comprise water, or a combination of water and one or more water soluble or dispersible ingredients. Hydrophilic liquid carriers comprising water are preferred.

The hydrophilic liquid carrier component can comprise any dermatologically acceptable carrier within which the essential thickening agents, reflective particulate material, and optional other materials can be incorporated to enable the particulate material and optional components to be delivered to the skin at an appropriate concentration. The hydrophilic liquid carrier, thus, ensures that the particulate material is applied to and distributed evenly over the selected target at an appropriate concentration.

The carrier may contain one or more dermatologically acceptable semi-solid or liquid fillers, diluents, solvents, extenders and the like. Liquid carriers can also include gel materials. Preferred carriers are substantially liquid. The carrier can itself be inert or it can possess dermatological benefits of its own. Concentrations of the hydrophilic liquid carrier can vary with the carrier selected and the intended concentrations of the essential and optional components.

Suitable hydrophilic carriers include conventional or otherwise known carriers that are dermatologically acceptable. The carrier should also be physically and chemically compatible with the essential components described herein, and should not unduly impair stability, efficacy or other use benefits associated with the compositions of the present invention. Preferred components of the compositions of this invention should be capable of being commingled in a manner such that there is no interaction which would substantially reduce the efficacy of the composition under ordinary use situations.

The type of hydrophilic carrier utilized in the present invention depends on the type of product form desired for the composition. The topical compositions useful in the subject invention may be made into a wide variety of product forms such as are known in the art. These include, but are not limited to, lotions, creams, gels, sprays, pastes, mousses and cosmetics (e.g., semi-solid or liquid make-up, including foundations, eye-makeup, pigmented or non-pigmented lip treatments and the like). These product forms may comprise several types of carriers including, but not limited to, solutions, aerosols, emulsions, gels, and liposomes.

Preferred hydrophilic carriers can contain a dermatologically acceptable, non-aqueous hydrophilic diluent. Nonlimiting examples of hydrophilic diluents are organic hydrophilic diluents such as lower monovalent alcohols (e.g., $C_1$–$C_4$) and low molecular weight glycols and polyols, including propylene glycol, polyethylene glycol (e.g., Molecular Weight 200–600 g/mole), polypropylene glycol (e.g., Molecular Weight 425–2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

As described hereafter, the hydrophilic liquid carrier may contain a wide variety of water-soluble or water miscible optional ingredients which can perform one or more skin conditioning or skin treating functions. Compositions containing a hydrophilic liquid carrier component, which is thickened and which contains the dispersed charged reflective particulate materials, may also comprise a hydrophobic phase resulting in the product form of emulsions. Compositions with both a hydrophilic phase and a hydrophobic phase are also described hereinafter.

II. Polymeric Thickening Agent

The compositions of the present invention also comprise a polymeric thickening agent. The polymeric thickening agent comprises from about 0.01% to about 10%, preferably from about 0.1% to about 5%, and more preferably from about 0.25% to about 2%, by weight of the composition. The polymeric thickening agent serves to increase the viscosity of the hydrophilic liquid carrier help disperse or suspend the charged reflective particulate material in the hydrophilic liquid carrier. In addition, the polymeric thickening agent also improves the aesthetics of the composition, e.g., good feel, nongreasiness, easy spreading, etc.

Nonlimiting types of preferred thickening agents suitable for use in the compositions herein include the following:

A. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. The preferred carboxylic acid polymers are of two general types. The first type of polymer is a crosslinked homopolymer of an acrylic acid monomer or derivative thereof (e.g., wherein the acrylic acid has substituents on the two and three carbon positions independently selected from the group consisting of $C_{1-4}$ alkyl, —CN, —COOH, and mixtures thereof). The second type of polymer is a crosslinked copolymer having a first monomer selected from the group consisting of an acrylic acid monomer or derivative thereof (as just described in the previous sentence), a short chain alcohol (i.e., a $C_{1-4}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof), and mixtures thereof; and a second monomer which is a long chain alcohol (i.e. $C_{8-40}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof). Combinations of these two types of polymers are also useful herein.

In the first type of crosslinked homopolymers, the monomers are preferably selected from the group consisting of acrylic acid, methacrylic acid, ethacrylic acid, and mixtures thereof, with acrylic acid being most preferred. In the second type of crosslinked copolymers the acrylic acid monomer or derivative thereof is preferably selected from the group consisting of acrylic acid, methacrylic acid, ethacrylic acid, and mixtures thereof, with acrylic acid, methacrylic acid, and mixtures thereof being most preferred. The short chain alcohol acrylate ester monomer or derivative thereof is preferably selected from the group consisting of $C_{1-4}$ alcohol acrylate esters, $C_{1-4}$ alcohol methacrylate esters, $C_{1-4}$ alcohol ethacrylate esters, and mixtures thereof, with the $C_{1-4}$ alcohol acrylate esters, $C_{1-4}$ alcohol methacrylate esters, and mixtures thereof, being most preferred. The long chain alcohol acrylate ester monomer is selected from $C_{8-40}$ alkyl acrylate esters, with $C_{10-30}$ alkyl acrylate esters being preferred.

The crosslinking agent in both of these types of polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinkers are those selected from the group consisting of allyl ethers of sucrose and allyl ethers of pentaerythritol, and mixtures thereof. These polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are both incorporated by reference herein in their entirety. See also, *CTFA International Cosmetic Ingredient Dictionary*, fourth edition, 1991, pp. 12 and 80; which are also incorporated herein by reference in their entirety.

Examples of commercially available homopolymers of the first type useful herein include the carbomers, which are homopolymers of acrylic acid crosslinked with allyl ethers of sucrose or pentaerytritol. The carbomers are available as the Carbopol® 900 series from B. F. Goodrich (e.g., Carbopol® 954). Examples of commercially available copolymers of the second type useful herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/C10–30 alkyl acrylate crosspolymers and are commercially available as Carbopol® 1342, Carbopol® 1382Pemulen TR-1, and Pemulen TR-2, from B. F. Goodrich. In other words, examples of carboxylic acid polymer thickeners useful herein are those selected from the group consisting of carbomers, acrylates/C10–C30 alkyl acrylate crosspolymers, and mixtures thereof.

B. Crosslinked Polyacrylate Polymers

The crosslinked polyacrylate polymers useful as thickeners or gelling agents include both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987; all of which are incorporated by reference herein in their entirety.

The crosslinked polyacrylate polymers are high molecular weight materials that can be characterized by the general formula: $(A)_l(B)_m(C)_n$ and comprise the monomer units $(A)_l$, $(B)_m$, and $(C)_n$, wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is a monomer that is polymerizable with (A) or (B), for example a monomer having a carbon-carbon double bond or other such polymerizable functional group, l is an integer of 0 or greater, m is an integer of 0 or greater, n is an integer of 0 or greater, but where either l or m, or both, must be 1 or greater.

The (C) monomer can be selected from any of the commonly used monomers. Nonlimiting examples of these monomers include ethylene, propylene, butylene, isobutylene, eicosene, maleic anhydride, acrylamide, methacrylamide, maleic acid, acrolein, cyclohexene, ethyl vinyl ether, and methyl vinyl ether. In the cationic polymers of the present invention, (C) is preferably acrylamide. The alkyl portions of the (A) and (B) monomers are short chain length alkyls such as $C_1-C_8$, preferably $C_1-C_5$, more preferably $C_1-C_3$, and most preferably $C_1-C_2$. When quaternized, the polymers are preferably quaternized with short chain alkyls, i.e., $C_1-C_8$, preferably $C_1-C_5$, more preferably $C_1-C_3$, and most preferably $C_1-C_2$. The acid addition salts refer to polymers having protonated amino groups. Acid addition salts can be performed through the use of halogen (e.g. chloride), acetic, phosphoric, nitric, citric, or other acids.

These $(A)_l(B)_m(C)_n$ polymers also comprise a crosslinking agent, which is most typically a material containing two or more unsaturated functional groups. The crosslinking agent is reacted with the monomer units of the polymer and is incorporated into the polymer thereby forming links or covalent bonds between two or more individual polymer chains or between two or more sections of the same polymer chain. Nonlimiting examples of suitable crosslinking agents include those selected from the group consisting of methylenebisacrylamides, diallyldialkyl ammonium halides, polyalkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, divinyl benzene, divinyl naphthalene, ethyl vinyl ether, methyl vinyl ether, and allyl acrylate. Other crosslinkers include formaldehyde and glyoxal. Preferred for use herein as a crosslinking agent is methylenebisacrylamide.

Widely varying amounts of the crosslinking agent can be employed depending upon the properties desired in the final polymer, e.g. viscosifying effect. Without being limited by theory, it is believed that incorporation of a crosslinking agent into these cationic polymers provides a material that is a more effective viscosifying agent without negatives such as stringiness and viscosity breakdown in the presence of electrolytes. The crosslinking agent, when present, can comprise from about 1 ppm to about 1000 ppm, preferably from about 5 ppm to about 750 ppm, more preferably from about 25 ppm to about 500 ppm, even more preferably from about 100 ppm to about 500 ppm, and most preferably from about 250 ppm to about 500 ppm of the total weight of the polymer on a weight/weight basis.

The intrinsic viscosity of the crosslinked polymer, measured in one molar sodium chloride solution at 25° C., is generally above 6, preferably from about 8 to about 14. The molecular weight (weight average) of the crosslinked polymers hereof is high, and is believed to typically be between about 1 million and about 30 million. The specific molecular weight is not critical and lower or higher weight average molecular weights can be used as long as the polymer retains its intended viscosifying effects. Preferably, a 1.0% solution of the polymer (on an actives basis) in deionized water will have a viscosity at 25° C. of at least about 20,000 cP, preferably at least about 30,000 cP, when measured at 20 RPM by a Brookfield RVT (Brookfield Engineering Laboratories, Inc. Stoughton, Mass., USA).

These cationic polymers can be made by polymerization of an aqueous solution containing from about 20% to about 60%, generally from about 25% to about 40%, by weight monomer, in the presence of an initiator (usually redox or thermal) until the polymerization terminates. The crosslinking agent can also be added to the solution of the monomers to be polymerized, to incorporate it into the polymer. In the polymerization reactions, the temperature generally starts between about 0° and 95° C. The polymerization can be conducted by forming a reverse phase dispersion of an aqueous phase of the monomers (and also any additional crosslinking agents) into a nonaqueous liquid, e.g. mineral oil, lanolin, isododecane, oleyl alcohol, and other volatile and nonvolatile esters, ethers, and alcohols, and the like.

All percentages describing the polymer in this section of the description herein are molar, unless otherwise specified. When the polymer contains (C) monomer, the molar proportion of (C) monomer, based on the total molar amount of (A), (B), and (C), can be from 0% to about 99%. The molar proportions of (A) and (B) can each be from 0% to 100%. When acrylamide, is used as the (C) monomer, it will preferably be used at a level of from about 20% to about 99%, more preferably from about 50% to about 90%.

Where monomer (A) and (B) are both present, the ratio of monomer (A) to monomer (B) in the final polymer, on a molar basis, is preferably from about 99:5 to about 15:85, more preferably from about 80:20 to about 20:80. Alternatively, in another class of polymers, the ratio is from about 5:95 to about 50:50, preferably from about 5:95 to about 25:75.

In another alternative class of polymers, the ratio (A):(B) is from about 50:50 to about 85:15. Preferably the ratio (A):(B) is about 60:40 to about 85:15, most preferably about 75:25 to about 85:15.

Most preferred is where monomer (A) is not present and the ratio of monomer (B):monomer (C) is from about 30:70 to about 70:30, preferably from about 40:60 to about 60:40 and most preferably from about 45:55 to about 55:45.

Cationic polymers that are useful herein that are especially preferred are those conforming to the general structure $(A)_l(B)_m(C)_n$ wherein l is zero, (B) is methyl quaternized dimethylaminoethyl methacrylate, the ratio of (B):(C) is from about 45:55 to about 55:45, and the crosslinking agent is methylenebisacrylamide. An example of such a cationic polymer is one that is commercially available as a mineral oil dispersion (which can also include various dispersing aids such as PPG-1 trideceth-6) under the trademark Salcare® SC92 from Allied Colloids Ltd. (Norfolk, Va.). This polymer has the proposed CTFA designation, "Polyquaternium 32 (and) Mineral Oil".

Other cationic polymers useful herein, are those not containing acrylamide or other (C) monomers, that is, n is zero. In these polymers the (A) and (B) monomer components are as described above. An especially preferred group of these non-acrylamide containing polymers is one in which l is also zero. In this instance the polymer is essentially a homopolymer of a dialkylaminoalkyl methacrlyate monomer or its quaternary ammonium or acid addition salt. These diaklylaminoalkyl methacrylate polymers preferably contain a crosslinking agent as described above.

A cationic polymer, which is essentially a homopolymer, useful herein is one conforming to the general structure $(A)_l(B)_m(C)_n$ wherein l is zero, (B) is methyl quaternized dimethylaminoethyl methacrylate, n is zero, and the crosslinking agent is methylenebisacrylamide. An example of such a homopolymer is commercially available as a mixture containing approximately 50% of the polymer, approximately 44% mineral oil, and approximately 6% PPG-1 trideceth-6 as a dispersing aid, from Allied Colloids Ltd, (Norfolk, Va.) under the trademark Salcare® SC95. This polymer has recently been given the CTFA designation "Polyquaternium 37 (and) Mineral Oil (and) PPG-1 Trideceth-6".

C. Polyacrylamide Polymers

Also useful herein as thickening agents are polyacrylamide polymers, especially non-ionic polyacrylamide polymers including substituted branched or unbranched polymers. These polymers can be formed from a variety of monomers including acrylamide and methacrylamide which are unsubstituted or substituted with one or two alkyl groups (preferably $C_1$ to $C_5$). Preferred are acrylate amide and methacrylate amide monomers in which the amide nitrogen is unsubstituted, or substituted with one or two $C_1$ to $C_5$ alkyl groups (preferably methyl, ethyl, or propyl), for example, acrylamide, methacrylamide, N-methacrylamide, N-methylmethacrylamide, N,N-dimethylmethacrylamide, N-isopropylacrylamide, N-isopropylmethacrylamide, and N,N-dimethylacrylamide. These polymers have a molecular weight greater than about 1,000,000 preferably greater than about 1,5000,000 and range up to about 30,000,000. Most preferred among these polyacrylamide polymers is the non-ionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

D. Polysaccharides

A wide variety of polysaccharides are useful herein as thickening agents. By "polysaccharides" are meant gelling agents containing a backbone of repeating sugar (i.e. carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a C10–C30 straight chain or branched chain alkyl group through an ether linkage. Typically these polymers are ethers of C10–C30 straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1→3) linked glucose units with a (1→6) linked glucose every three units, a commercially available example of which is Clearogel™ CS11 from Michel Mercier Products Inc. (Mountainside, N.J.).

E. Gums

Other additional thickening and gelling agents useful herein include materials which are primarily derived from natural sources. Nonlimiting examples of these gelling agent gums include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

E. Crosslinked Vinyl Ether/Maleic Anhydride Copolymers

Other additional thickening and gelling agents useful herein include crosslinked copolymers of alkyl vinyl ethers and maleic anhydride. In these copolymers the vinyl ethers are represented by the formula R–O–CH==CH$_2$ wherein R is a C1–C6 alkyl group, preferably R is methyl. Preferred crosslinking agents are C4–C20 dienes, preferably C6 to C16 dienes, and most preferably C8 to C12 dienes. A particularly preferred copolymer is one formed from methyl vinyl ether and maleic anhydride wherein the copolymer has been crosslinked with decadiene, and wherein the polymer when diluted as a 0.5% aqueous solution at pH 7 at 25° C. has a viscosity of 50,000–70,000 cps when measured using a Brookfield RTV viscometer, spindle #7 at 10 rpm. This copolymer has the CTFA designation PVM/MA decadiene crosspolymer and is commercially available as Stabilezer™ 06 from International Specialty Products (Wayne N.J.).

G. Crosslinked poly(N-vinylpyrrolidones)

Crosslinked polyvinyl(N-pyrrolidones) additionally useful herein as thickening and gelling agents include those described in U.S. Pat. No. 5,139,770, to Shih et al, issued Aug. 18, 1992, and U.S. Pat. No. 5,073,614, to Shih et al., issued Dec. 17, 1991, both patents of which are incorporated by reference herein in their entirety. These gelling agents typically contain from about 0.25% to about 1% by weight of a crosslinking agent selected from the group consisting of divinyl ethers and diallyl ethers of terminal diols containing from about 2 to about 12 carbon atoms, divinyl ethers and diallyl ethers of polyethylene glycols containing from about 2 to about 600 units, dienes having from about 6 to about 20 carbon atoms, divinyl benzene, vinyl and allyl ethers of pentaerythritol, and the like. Typically, these gelling agents have a viscosity from about 25,000 cps to about 40,000 cps when measured as a 5% aqueous solution at 25° C. using a Brookfield RVT viscometer with Spindle #6 at 10 rpm. Commercially available examples of these polymers include ACP-1120, ACP-1179, and ACP-1180, available from International Specialty Products (Wayne, N.J.).

Thickening agents which are suitable for use herein also include those disclosed in U.S. Pat. No. , 4,387,107, to Klein et al., issued June 7, 1983 and "Encyclopedia of Polymer and Thickeners for Cosmetics," R. Y. Lochhead and W. R. Fron, eds., Cosmetics & Toiletries, vol. 108, pp. 95–135 (May 1993), which are all incorporated herein by reference in their entirety.

Preferred compositions of the present invention include a thickening agent selected from the group consisting of carboxylic acid polymers, acrylates/$C_{10}$–$C_{30}$ alkyl acrylate crosspolymers, polyacrylamide polymers, and mixtures thereof. Generally, the thickening agent used to thicken the hydrophilic liquid carrier will preferably not be used in the acid form since acidic thickeners can interact with the charged reflective particulate material suspended or dispersed within the thickened hydrophilic phase. Alternatively, if the acid form of the thickening agents are used, the composition can be neutralized to a pH range described hereinafter before addition of the charged reflective particulate material. Generally, the pH of the thickened hydrophilic liquid carrier will range from about 4 to about 8.5, preferably from about 4.5 to about 8, more preferably from about 5 to 8, and most preferably from about 6 to 8.

III. Charged Particulate Material

The compositions of the present invention also essentially comprise from about 0.01% to about 2%, preferably from about 0.05% to about 1.5%, more preferably from about 0.1% to about 1%, by weight of the composition, of a charged particulate material dispersed throughout the thickened hydrophilic carrier. The charged particulate material will preferably comprise a metallic oxide which is coated with a coating material that confers a net charge that is greater than the zeta potential of the uncoated metallic oxide.

Without being limited by theory, it is believed that reflective particulate materials, such as $TiO_2$, generally possess relatively high surface activity, creating formulation instabilities discussed hereinbefore, e.g., with polymeric thickening agents. In addition, these particulate materials have a tendency to agglomerate, e.g., clump together. These problems can be solved by coating the metallic oxide with a coating material that confers a net charge that is greater than the zeta potential of the uncoated reflective particulate material. Typically, the coating material confers a zeta potential that is greater than about ±20 mV (e.g., either in the positive or negative direction) at pH from about 4 to about 8.5. This provides formulation stability and prevents agglomeration of the reflective particulate materials. Particulates and their charges are well known to those of ordinary skill in the art, and are well described in R. J Hunter, *Zeta Potential in Colloid Science: Principles and Application* (1981), published by Academic Press; J. N. Israelachvili, *Intermolecular and Surface Forces: With Applications to Colloidal and Biological Systems* (1985), published by Academic Press; and Hoogeven, N. G. et al., *Colloids and Surfaces*, Physiochemical and Engineering Aspects, Vol. 117, p. 77 (1966). All of these publications are incorporated herein by reference in their entirety.

Preferably, the particulates all have a net cationic charge or a net anionic charge. It is believed that because all of the particles have the same charge, the repulsive forces prevent agglomeration and induce even distribution throughout the hydrophilic phase. As a result, (i) lower concentrations of the reflective particulate material can be used to obtain acceptable degrees of skin coverage, (ii) the composition aesthetics are increased, and (iii) formulation instabilities are decreased. Thus, the use of charged particulates provide efficient coverage at relatively low levels of the reflective particulate materials.

The charged particulate material useful in the compositions of the present invention will generally have a refractive index of at least about 2, more preferably at least about 2.5, e.g., from about 2 to about 3. Refractive index can be determined by conventional methods. For example, a method for determining the refractive index which is applicable to the present invention is described in J. A. Dean, Ed., *Lange's Handbook of Chemistry*, 14th Ed., McGraw Hill, New York, 1992, Section 9, Refractometry, incorporated herein by reference in its entirety.

Preferred particulate materials are those having an primary particle size of from about 100 nm to about 300 nm, more preferably from about 100 to about 250 nm in the neat form (i.e., in the essentially pure, powder form prior to combination with any carrier). Preferred particulate materials have a primary particle size when dispersed in the composition of from about 100 nm to about 1000 nm, more preferably from about 100 nm to about 400 nm, even more preferably from about 200 nm to about 300 nm. Primary particle size can be determined using the ASTM Designation E20-85 "Standard Practice for Particle Size Analysis of Particulate Substances in the Range of 0.2 to 75 Micrometers by Optical Microscopy", ASTM Volume 14.02, 1993, incorporated herein by reference.

The particles may have a variety of shapes, including spherical, spheroidal, elliptical, lamellar, irregular, needle and rod-like, provided that the desired refractive index is provided. The particulate can be in a variety of physical forms, including rutile, anatase or a combination thereof.

A. Metallic Oxide

The reflective particulate material preferably comprises particles of inorganic material comprising $TiO_2$, ZnO, $ZrO_2$ and combinations thereof, more preferably $TiO_2$, ZnO and combinations thereof (combinations are intended to include particles which comprise one or more of these materials, as well as mixtures of these particulate materials) and most preferably, the particles consist essentially of $TiO_2$. The particulate material may be a composite, e.g., deposited on a core or mixed with other materials such as, but not limited to, silica, silicone resin, mica, and nylon.

Inorganic particulate materials, e.g., comprising $TiO_2$, ZnO or $ZrO_2$ are commercially available from a number of sources. One example of a suitable particulate material comprises the material available from U.S. Cosmetics (TRONOX $TiO_2$ series, SAT-T CR837, a rutile $TiO_2$).

The compositions may contain other inorganic or organic particulate materials. However, it is preferred that the particulates in the compositions of the invention consist essentially of the particulate material described in this section.

B. Coating Material

The reflective particulate materials described hereinbefore are preferably coated with a coating material that confers a net charge that is greater than the zeta potential of the uncoated reflective particulate material. Therefore, any coating material can be used as long as the net charge (cationic or anionic) conferred to the reflective particulate is greater than the untreated reflective particulate material. However, all of the particulates within a composition are preferably treated with the same net charge, e.g., no mixing of cationic and anionic coating materials, to benefit from the repulsive forces between the reflective particulates. It is understood to one skilled in the art, however, that small amounts of oppositely charged coating materials may be used, as long as, the overall repulsive forces are maintained.

Nonlimiting examples of coating materials that confer a cationic charge include cationic polymers (natural and/or synthetic) and cationic surfactants. Preferred cationic coating materials are selected from the group consisting of chitosan, hydroxypropyl chitosan, quaternium-80, polyquaternium-7, and mixtures thereof.

Nonlimiting examples of coating materials that confer an anionic charge include anionic polymers (natural and/or synthetic) and anionic surfactants. Preferred anionic coating materials are selected from the group consisting of ammonium polyacrylate, sodium polyacrylate, potassium polyacrylate, ethylene acrylic acid copolymer, hydrolyzed wheat protein polysiloxane copolymer, dimethicone copolyol phosphate, dimethicone copolyol acetate, dimethicone copolyol laurate, dimethicone copolyol stearate, dimethicone copolyol behenate, dimethicone copolyol isostearate, dimethicone copolyol hydroxystearate, phosphate ester, sodium chondroiton sulfate, sodium hyaluronate, ammonium hyaluronate, sodium algenate, ammonium algenate, ammonium laurate, sodium laurate, potassium laurate, ammonium myristate, sodium myristate, potassium myristate, ammonium palmitate, sodium palmitate, potassium palmitate, ammonium stearate, sodium stearate, potassium stearate, ammonium oleate, sodium oleate, potassium oleate, and mixtures thereof. More preferred are anionic coating materials selected from the group consisting of ammonium polyacrylate, sodium polyacrylate, and mixtures thereof.

The charged particulate materials (e.g., treated with the coating material) are available in essentially neat, powdered form, or predispersed in various types of carriers, including but not limited to water, organic hydrophilic diluents such as lower monovalent alcohols (e.g., $C_1$–$C_4$) and low molecular weight glycols and polyols, including propylene glycol, polyethylene glycol (e.g., Molecular Weight 200–600 g/mole), polypropylene glycol (e.g., Molecular Weight 425–2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof. Preferably, the charged particulate materials are predispersed in water, glycerin, butylene glycol, propylene glycol, and mixtures thereof. Examples of commercially available charged particulate materials include Kobo BG65CA (a predispersion of ammonium polyacrylate treated $TiO_2$, butylene glycol, water, and ammonium zirconium carbonate), Kobo BG60DC (a predispersion of chitosan treated $TiO_2$ and butylene glycol), Kobo GLW75CA (a predispersion of ammonium polyacrylate treated $TiO_2$, water, glycerin, and ammonium zirconium carbonate), all available from Kobo Products Inc., located in South Plainfield, N.J.

IV. Optional Components

The skin care compositions of the present invention essentially contain only the thickened, particulate-containing hydrophilic liquid carrier. Preferably, however, the compositions herein, and especially those in the form of emulsions, will also contain a hydrophobic component or phase that can contain a variety of hydrophobic materials.

A. Hydrophobic Components

Compositions according to the present invention, such as emulsions, can contain a hydrophobic phase comprising a lipid, oil, oily or other hydrophobic component. The compositions of the present invention preferably comprise from about 1% to about 98%, preferably from about 1% to about 50%, and more preferably from about 1% to about 30% by weight of the composition of a hydrophobic component. The hydrophobic component may be derived from animals, plants, or petroleum and may be natural or synthetic (i.e., man-made). Preferred hydrophobic components are substantially water-insoluble, more preferably essentially water-insoluble. Preferred hydrophobic components are those having a melting point of about 25° C. or less under about one atmosphere of pressure.

A wide variety of suitable hydrophobic components are known and may be used herein and numerous examples can be found in Sagarin, *Cosmetics, Science and Technology*, 2nd Edition, Vol. 1, pp. 32–43 (1972), incorporated herein by reference. Nonlimiting examples of suitable hydrophobic components include those selected from the group consisting of:

(i) Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p.415–417 (1993), which are incorporated by reference herein in their entirety.

(ii) Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, *Drug. Cosmet. Ind.*, 89, 36–37, 76, 78–80, 82 (1961); and International Cosmetic Ingredient Dictionary, Fifth Edition, vol. 1, p. 537 (1993), which are incorporated by reference herein in their entirety.

(iii) Straight and branched chain hydrocarbons having from about 7 to about 40 carbon atoms. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). Also useful are the C7–C40 isoparaffins, which are C7–C40 branched hydrocarbons.

(iv) C1–C30 alcohol esters of C1–C30 carboxylic acids and of C2–C30 dicarboxylic acids, including straight and branched chain materials as well as aromatic derivatives (as used herein in reference to the hydrophobic component, mono- and poly- carboxylic acids include straight chain, branched chain and aryl carboxylic acids). Nonlimiting examples include diisopropyl sebacate, diisopropyl adipate, isopropyl myristate, isopropyl palmitate, methyl palmitate, myristyl propionate, 2-ethylhexyl palmitate, isodecyl neopentanoate, di-2-ethylhexyl maleate, cetyl palmitate, myristyl myristate, stearyl stearate, isopropyl stearate, methyl stearate, cetyl stearate, behenyl behenate, dioctyl maleate, dioctyl sebacate, diisopropyl adipate, cetyl octanoate, diisopropyl dilinoleate.

(v) Mono-, di- and tri- glycerides of C1–C30 carboxylic acids, e.g., caprylic/capric triglyceride, PEG-6 caprylic/capric triglyceride, PEG-8 caprylic/capric triglyceride.

(vi) Alkylene glycol esters of C1–C30 carboxylic acids, e.g., ethylene glycol mono- and di- esters, and propylene glycol mono- and di- esters of C1–C30 carboxylic acids e.,g., ethylene glycol distearate.

(vii) Propoxylated and ethoxylated derivatives of the foregoing materials.

(viii) C1–C30 mono- and poly- esters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

(ix) Organopolysiloxane oils. The organopolysiloxane oil may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Nonvolatile polysiloxanes are preferred. Nonlimiting examples of suitable silicones are disclosed in U.S. Pat. No. 5,069,897, to Orr, issued Dec. 3, 1991, which is incorporated by reference herein in its entirety. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Such polyalkylsiloxanes can be represented by the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Coming® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ where straight or branched chain alkyl having from two to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the composition include those represented by the chemical formula $[SiR_2-O]n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Coming® 345 fluid having a viscosity of 4.5 centistokes and a boiling point of 217°, which primarily contains a mixture of the cyclomethicone tetramer, pentamer, and hexamer (i.e. n=4, 5, and 6).

Also useful are materials such as trimethylsiloxysilicate, which is a polymeric material corresponding to the general chemical formula $[(CH_2)_3SiO_{1/2}]_x[SiO_2]y$, wherein x is an integer from about 1 to about 500 and y is an integer from about 1 to about 500. A commercially available trimethylsiloxysilicate is sold as a mixture with dimethicone as Dow Corning® 593 fluid.

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

(x) Vegetable oils and hydrogenated vegetable oils. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

(xi) Animal fats and oils, e.g., lanolin and derivatives thereof, cod liver oil.

(xii) Other materials: Also useful are C4–C20 alkyl ethers of polypropylene glycols, C1–C20 carboxylic acid esters of polypropylene glycols, and di-C8–C30 alkyl ethers. Nonlimiting examples of these materials include PPG-14 butyl ether, PPG-15 stearyl ether, dioctyl ether, dodecyl octyl ether, and mixtures thereof.

B. Emulsion Compositions

Compositions of the present invention which contain hydrophobic components as herebefore described are frequently fashioned in the form of emulsions. Emulsions comprise a hydrophilic phase comprising the thickened particulate-containing hydrophilic liquid carrier or other hydrophilic diluent, and a hydrophobic phase comprising a hydrophobic component, e.g., a lipid, oil or oily material. As well known to one skilled in the art, the hydrophilic phase will be dispersed in the hydrophobic phase, or vice versa, to form respectively hydrophilic or hydrophobic dispersed and continuous phases, depending on the composition ingredients. In emulsion technology, the term "dispersed phase" is a term well-known to one skilled in the art which means that the phase exists as small particles or droplets that are suspended in and surrounded by a continuous phase. The dispersed phase is also known as the internal or discontinues phase. The emulsion may be or comprise (e.g., in a triple or other multi-phase emulsion) an oil-in-water emulsion or a water-in-oil emulsion such as a water-in-silicone emulsion. Oil-in-water emulsions typically comprise from about 1% to about 50% (preferably about 1% to about 30%) of the dispersed hydrophobic phase and from about 1% to about 98% (preferably from about 40% to about 90%) of the continuous hydrophilic phase; water-in-oil emulsions typically comprise from about 1% to about 98% (preferably from about 40% to about 90%) of the dispersed hydrophilic phase and from about 1% to about 50% (preferably about 1% to about 30%) of the continuous hydrophobic phase. The emulsion may also comprise a gel network, such as described in G. M. Eccleston, *Application of Emulsion Stability Theories to Mobile and Semisolid O/W Emulsions*, Cosmetics & Toiletries, Vol. 101, November 1996, pp. 73–92, incorporated herein by reference. Preferred emulsions are further described below.

Preferred emulsions have an apparent viscosity of from about 5,000 to about 200,000 centipoise (cps). For example, preferred lotions have an apparent viscosity of from about 10,000 to about 40,000 cps; preferred creams have an apparent viscosity of from about 60,000 to about 160,000 cps. Apparent viscosity can be determined using a Brookfield DVII RV viscometer, spindle TC, at 5 rpm, or the equivalent thereof. The viscosity is determined on the composition after the composition has been allowed to stabilize following its preparation, generally at least 24 hours under conditions of 25° C.+/−1° C. and ambient pressure after preparation of the composition. Apparent viscosity is measured with the composition at a temperature of 25° C.+/−1° C., after 30 seconds spindle rotation.

The emulsion may contain an emulsifier and/or surfactant, generally to help disperse and suspend the discontinues phase within the continuous phase. A wide variety of such agents can be employed. Known or conventional emulsifiers/surfactants can be used in the composition, provided that the selected agent is chemically and physically compatible with essential components of the composition, and provides the desired dispersion characteristics. Suitable agents include nonsilicone-containing emulsifiers/surfactants, silicone emulsifiers/surfactants, and mixtures thereof.

In a preferred embodiment, the compositions herein comprise a hydrophilic emulsifier or surfactant. The compositions of the present invention preferably comprise from about 0.05% to about 5%, more preferably from about 0.05% to about 1% of at least one hydrophilic surfactant. Without intending to be limited by theory, it is believed that the hydrophilic surfactant assists in dispersing hydrophobic materials, e.g., hydrophobic structuring agents, in the hydrophilic phase. The surfactant, at a minimum, must be hydrophilic enough to disperse in the hydrophilic phase. Preferred surfactants are those having an HLB of at least about 8. The exact surfactant chosen will depend upon the pH of the composition and the other components present.

Preferred hydrophilic surfactants are selected from nonionic surfactants. Among the nonionic surfactants that are useful herein are those that can be broadly defined as condensation products of long chain alcohols, e.g. C8–30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e. alkylene oxide esters of fatty acids). These materials have the general formula $RCO(X)_n OH$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 200. Other nonionic surfactants are the condensation products of alkylene oxides with 2 moles of fatty acids (i.e. alkylene oxide diesters of fatty acids). These materials have the general formula $RCO(X)_n OOCR$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 100. Other nonionic surfactants are the condensation products of alkylene oxides with fatty alcohols (i.e. alkylene oxide ethers of fatty alcohols). These materials have the general formula $R(X)_n OR'$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 100 and R' is H or a C10–30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_n OR'$ wherein R and R' are C10–30 alkyl groups, X is —OCH$_2$CH$_2$ (i.e. derived from ethylene glycol or oxide) or —OCH$_2$CHCH$_3$— (derived from propylene glycol or oxide), and n is an integer from about 6 to about 100. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, steareth-21, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2$ CO— moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

Preferred among the nonionic surfactants are those selected from the group consisting of steareth-21, ceteareth-20, ceteareth-12, sucrose cocoate, steareth-100, PEG-100 stearate, and mixtures thereof.

Other nonionic surfactants suitable for use herein include sugar esters and polyesters, alkoxylated sugar esters and polyesters, C1–C30 fatty acid esters of C1–C30 fatty alcohols, alkoxylated derivatives of C1–C30 fatty acid esters of C1–C30 fatty alcohols, alkoxylated ethers of C1–C30 fatty alcohols, polyglyceryl esters of C1–C30 fatty acids, C1–C30 esters of polyols, C1–C30 ethers of polyols, alkyl phosphates, polyoxyalkylene fatty ether phosphates, fatty acid amides, acyl lactylates, and mixtures thereof. Nonlimiting examples of these emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Another emulsifier useful herein are fatty acid ester blends based on a mixture of sorbitan or sorbitol fatty acid ester and sucrose fatty acid ester, the fany acid in each instance being preferably $C_8$–$C_{24}$, more preferably $C_{10}$–$C_{20}$. The preferred fatty acid ester emulsifier is a blend of sorbitan or sorbitol $C_{16}$–$C_{20}$ fatty acid ester with sucrose $C_{10}$–$C_{16}$ fatty acid ester, especially sorbitan stearate and sucrose cocoate. This is commercially available from ICI under the trade name Arlatone 2121.

The hydrophilic surfactants useful herein can alternatively or additionally include any of a wide variety of cationic, anionic, zwitterionic, and amphoteric surfactants such as are known in the art. See, e.g., McCutcheon's, *Deteroents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Exemplary cationic surfactants useful herein include those disclosed in U.S. Pat. No. 5,151,209, to McCall et al., issued Sep. 29, 1992; U.S. Pat. No. 5,151,210, to Steuri et al., issued Sep. 29, 1992; U.S. Pat. No. 5,120,532, to Wells et al., issued Jun. 9, 1992; U.S. Pat. No. 4,387,090, to Bolich, issued Jun. 7, 1983; U.S. Pat. No. 3,155,591, Hilfer, issued Nov. 3, 1964; U.S. Pat. No. 3,929,678, to Laughlin et al., issued Dec. 30, 1975; U.S. Pat. No. 3,959,461, to Bailey et al., issued May 25, 1976; *McCutcheon's, Detergents & Emulsifiers*, (North American edition 1979) M.C. Publishing Co.; and Schwartz, et al., *Surface Active Agents, Their Chemistry and Technology*, New York: lnterscience Publishers, 1949; all of these documents being incorporated herein by reference in their entirety. The cationic surfactants useful herein include cationic ammonium salts such as quaternary ammonium salts, and amino-amides.

A wide variety of anionic surfactants are also useful herein. See, e.g., U.S. Pat. No. 3,929,678, to Laughlin et al., issued Dec. 30, 1975, which is incorporated herein by reference in its entirety. Nonlimiting examples of anionic surfactants include the alkoyl isethionates (e.g., $C_{12}$–$C_{30}$), alkyl and alkyl ether sulfates and salts thereof, alkyl and alkyl ether phosphates and salts thereof, alkyl methyl taurates (e.g., $C_{12}$–$C_{30}$), and soaps (e.g., alkali metal salts, e.g., sodium or potassium salts) of fatty acids.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$–$C_{18}$) and one contains an anionic water solubilizing group, e.g., carboxy, sulfonate, sulfate, phosphate, or phosphonate. Examples are alkyl imino acetates, and iminodialkanoates and aminoalkanoates, imidazolinium and ammonium derivatives. Other suitable amphoteric and zwitterionic surfactants are those selected from the group consisting of betaines, sultaines, hydroxysultaines, alkyl sarcosinates (e.g., $C_{12}$–$C_{30}$), and alkanoyl sarcosinates.

Emulsions of the present invention can include a silicone containing emulsifier or surfactant. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2–C30 pendant side chains. Still other useful dimethicone copolyols include materials having various cationic, anionic, amphoteric, and zwitterionic pendant moieties.

The dimethicone copolyol emulsifiers useful herein can be described by the following general structure:

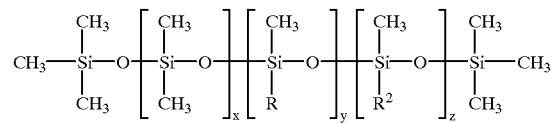

wherein R is C1–C30 straight, branched, or cyclic alkyl and $R^2$ is selected from the group consisting of —$(CH_2)n$—O—$(CH_2CHR^3O)m$—H, and —$(CH_2)n$—O—$(CH_2CHR^3O)m$—$(CH_2CHR^4O)_o$—H, wherein n is an integer from 3 to about 10; $R^3$ and $R^4$ are selected from the group consisting of 11 and C1–C6 straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is:

—$(CH_2)_n$—O—$R^5$, wherein $R^5$ is a cationic, anionic, amphoteric, or zwitterionic moiety.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2–C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See *International Cosmetic Inttredient Dictionary*, Fifth Edition, 1993, which is incorporated by reference herein in its entirety.

Dimethicone copolyol emulsifiers useful herein are described, for example, in U.S. Pat. No. 4,960,764, to Figueroa, Jr. et al., issued Oct. 2, 1990; European Patent No. EP 330,369, to SaNogueira, published Aug. 30, 1989; G. H. Dahms, et al., "New Formulation Possibilities Offered by Silicone Copolyols," *Cosmetics & Toiletries*, vol. 110, pp. 91–100, March 1995; M. E. Carlotti et al., "Optimization of W/O-S Emulsions And Study Of The Quantitative Relationships Between Ester Structure And Emulsion Properties," *J. Dispersion Science And Technology*, 13(3), 315–336 (1992); P. Hameyer, "Comparative Technological Investigations of Organic and Organosilicone Emulsifiers in Cosmetic Water-in-Oil Emulsion Preparations," HAPPI 28(4), pp. 88–128 (1991); J. Smid-Korbar et al., "Efficiency and usability of silicone surfactants in emulsions," *Provisional Communication, International Journal of Cosmetic Science*, 12, 135–139 (1990); and D. G. Krzysik et al., "A New Silicone Emulsifier For Water-in-Oil Systems," *Drug and Cosmetic Industry*, vol. 146(4) pp. 28–81 (April 1990); incorporated by reference herein in their entirety.

C. Functional Optional Ingredients

The compositions herein may contain a wide variety of optional ingredients that perform one or more functions useful in products of this type. Such optional components may be found in either the thickened hydrophilic phase or the optional hydrophobic phase(s) or in one or more additional phases of the compositions herein. Nonexclusive examples of such materials are described in *Harry's Cosmeticoloy*, 7th Ed., Harry & Wilkinson (Hill Publishers, London 1982); in *Pharmaceutical Dosage Forms- Disperse Systems*; Lieberman, Rieger & Banker, Vols. 1 (1988) & 2 (1989); Marcel Decker, Inc.; in *The Chemistry and Manufacture of Cosmetics*, 2nd. Ed., deNavarre (Van Nostrand 1962–1965); and in *The Handbook of Cosmetic Science and Technology*, 1st Ed. Knowlton & Pearce (Elsevier 1993). Such ingredients include, but are not limited to, transparent particulates; skin conditioning agents such as emollients, humectants, and moisturizers; skin cleansers; skin care actives such as vitamin B3 compounds, retinoids, anti-oxidants/radical scavengers, and organic hydroxy acids; structuring agents; and other actives including anti-inflammatory agents, sunscreens/sunblocks, chelators, desquamation agents/exfoliants, and skin lightening agents. Each of these functional optional ingredients is described in detail as follows:

1. Transparent Particles: A safe and effective amount of a transparent particle may be added to the compositions of the subject invention, preferably from about 0.1% to about 15%, more preferably from about 0.2% to about 5%, and most preferable from about 0.3% to about 2.5%. The transparent particles have a refractive index of less then about 2.0. These particles diffuse light instead of reflecting light. Nonlimiting examples include mica, silica, nylon, polyethylene, talc, styrene, polypropylene, ethylene/acrylic acid copolymer, sericite, aluminum oxide, silicone resin, barium sulfate, calcium carbonate, cellulose acetate, polymethyl methacrylate, and mixtures thereof. Nonlimiting examples of commercially available transparent particles include Kobo MSS-500 silica; Kobo EA-209 (ethylene/acrylic acid copolymer); and M-102-Mica available from U.S. Cosmetic Corp., located in Dayville, Conn.

These transparent particles can also be treated with various treatments or made into a variety of composites to provide desired characteristics. A nonlimiting example of a commercially available composite transparent particle is Naturaleaf powder® (composite of mica, barium sulfate, and $TiO_2$), available from EM Industries, located in Hawthorne, N.Y.

2. Skin Care Active: In a preferred embodiment, the composition also includes an active useful for chronically regulating skin condition. Such materials are those which manifest skin appearance benefits following chronic application of the composition containing such materials. Materials having this effect include, but are not limited to, Vitamin $B_3$ compounds and retinoids. Other types of skin care actives include anti-oxidants/radical scavengers and organic hydroxy acids.

Specific examples of skin care actives include the following.

(i) Vitamin $B_3$ Compounds: In a preferred embodiment, the compositions of the present invention comprise a safe and effective amount of a vitamin $B_3$ compound. The vitamin $B_3$ compound enhances the skin appearance benefits of the present invention, especially in regulating skin condition, including regulating signs of skin aging, more especially wrinkles, lines, and pores. The compositions of the present invention preferably comprise from about 0.01% to about 50%, more preferably from about 0.1% to about 10%, even more preferably from about 0.5% to about 10%, and still more preferably from about 1% to about 5%, most preferably from about 2% to about 5%, of the vitamin B, compound As used herein, "vitamin $B_3$ compound" means a compound having the formula:

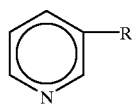

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Suitable esters of nicotinic acid include nicotinic acid esters of $C_1$–$C_{22}$, preferably $C_1$–$C_{16}$, more preferably $C_1$–$C_6$ alcohols. The alcohols are suitably straight-chain or branched chain, cyclic or acyclic, saturated or unsaturated (including aromatic), and substituted or unsubstituted. The esters are preferably non-vasodilating. As used herein, "non-vasodilating" means that the ester does not commonly yield a visible flushing response after application to the skin in the subject compositions (the majority of the general population would not experience a visible flushing response, although such compounds may cause vasodilation not visible to the naked eye, i.e., the ester is nonrubifacient). Non-vasodilating esters of nicotinic acid include tocopherol nicotinate and inositol hexanicotinate; tocopherol nicotinate is preferred.

Other derivatives of the vitamin $B_3$ compound are derivatives of niacinamide resulting from substitution of one or more of the amide group hydrogens. Nonlimiting examples of derivatives of niacinamide useful herein include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., C1–C 18). Specific examples of such derivatives include nicotinuric acid ($C_8H_8N_2O_3$) and nicotinyl hydroxamic acid ($C_6H_6N_2O_2$), which have the following chemical structures:

nicotinuric acid:

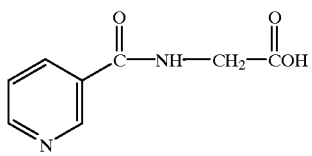

nicotinyl hydroxamic acid:

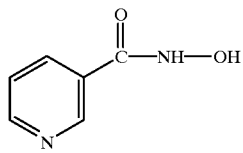

Exemplary nicotinyl alcohol esters include nicotinyl alcohol esters of the carboxylic acids salicylic acid, acetic acid, olycolic acid, palmitic acid and the like. Other non-limiting examples of vitamin $B_3$ compounds useful herein are 2-chloronicotinamide, 6-aminonicotinamide, 6-methylnicotinamide, n-methyl-nicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl) urea, 2-mercaptonicotinic acid, nicomol, and niaprazine.

Examples of the above vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

One or more vitamin $B_3$ compounds may be used herein. Preferred vitamin $B_3$ compounds are niacinamide and tocopherol nicotinate. Niacinamide is more preferred.

When used, salts, derivatives, and salt derivatives of niacinamide are preferably those having substantially the same efficacy as niacinamide in the methods of regulating skin condition described herein.

Salts of the vitamin B3 compound are also useful herein. Nonlimiting examples of salts of the vitamin $B_3$ compound useful herein include organic or inorganic salts, such as inorganic salts with anionic inorganic species (e.g., chloride, bromide, iodide, carbonate, preferably chloride), and organic carboxylic acid salts (including mono-, di- and tri-C1–C18 carboxylic acid salts, e.g., acetate, salicylate, glycolate, lactate, malate, citrate, preferably monocarboxylic acid salts such as acetate). These and other salts of the vitamin B3 compound can be readily prepared by the skilled artisan, for example, as described by W. Wenner, "The Reaction of L-Ascorbic and D-losascorbic Acid with Nicotinic Acid and Its Amide", J. Organic Chemistry, Vol. 14, 22–26 (1949), which is incorporated herein by reference. Wenner describes the synthesis of the ascorbic acid salt of niacinamide.

In a preferred embodiment, the ring nitrogen of the vitamin $B_3$ compound is substantially chemically free (e.g., unbound and/or unhindered), or after delivery to the skin becomes substantially chemically free ("chemically free" is hereinafter alternatively referred to as "uncomplexed"). More preferably, the vitamin $B_3$ compound is essentially uncomplexed. Therefore, if the composition contains the vitamin $B_3$ compound in a salt or otherwise complexed form, such complex is preferably substantially reversible, more preferably essentially reversible, upon delivery of the composition to the skin. For example, such complex should be substantially reversible at a pH of from about 5.0 to about 6.0. Such reversibility can be readily determined by one having ordinary skill in the art.

More preferably the vitamin $B_3$ compound is substantially uncomplexed in the composition prior to delivery to the skin. Exemplary approaches to minimizing or preventing the formation of undesirable complexes include omission of materials which form substantially irreversible or other complexes with the vitamin $B_3$ compound, pH adjustment, ionic strength adjustment, the use of surfactants, and formulating wherein the vitamin $B_3$ compound and materials which complex therewith are in different phases. Such approaches are well within the level of ordinary skill in the art.

Thus, in a preferred embodiment, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably essentially free of the salt form. The vitamin $B_3$ compound in the compositions hereof having a pH of from about 4 to about 7 typically contain less than about 50% of the salt form.

The vitamin $B_3$ compound may be included as the substantially pure material, or as an extract obtained by suitable physical and/or chemical isolation from natural (e.g., plant) sources. The vitamin $B_3$ compound is preferably substantially pure, more preferably essentially pure.

(ii) Retinoids: In a preferred embodiment, the compositions of the present invention contain a retinoid. The retinoid enhances the skin appearance benefits of the present invention, especially in regulating skin condition, including regulating signs of skin aging, more especially wrinkles, lines, and pores.

As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$–$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. Nos. 4,677,120, issued Jun. 30, 1987 to Parish et al.; 4,885,311, issued Dec. 5, 1989 to Parish et al.; 5,049,584, issued Sep. 17, 1991 to Purcell et al.; 5,124,356, issued Jun. 23, 1992 to Purcell et al.; and Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). One or more retinoids may be used herein. Preferred retinoids are retinol, retinyl palmitate, retinyl acetate, retinyl proprionate, retinal and combinations thereof. More preferred are retinol and retinyl palmitate.

The retinoid may be included as the substantially pure material, or as an extract obtained by suitable physical and/or chemical isolation from natural (e.g., plant) sources. The retinoid is preferably substantially pure, more preferably essentially pure.

The compositions of this invention may contain a safe and effective amount of the retinoid, such that the resultant composition is safe and effective for regulating skin condition, preferably for regulating visible and/or tactile discontinuities in skin, more preferably for regulating signs of skin aging, even more preferably for regulating visible and/or tactile discontinuities in skin texture associated with skin aging. The compositions preferably contain from or about 0.005% to or about 2%, more preferably 0.01% to or about 2%, retinoid. Retinol is most preferably used in an amount of from or about 0.01% to or about 0.15%; retinol esters are most preferably used in an amount of from or about 0.01% to or about 2% (e.g., about 1%); retinoic acids are most preferably used in an amount of from or about 0.01% to or about 0.25%; tocopheryl-retinoate, adapalene, and tazarotene are most preferably used in an amount of from or about 0.01% to or about 2%.

In a preferred embodiment, the composition contains both a retinoid and a Vitamin $B_3$ compound. The retinoid is preferably used in the above amounts, and the vitamin $B_3$ compound is preferably used in an amount of from or about 0.1% to or about 10%, more preferably from or about 2% to or about 5%.

(iii) Anti-Oxidants/Radical Scavengers: Preferred compositions of the subject invention include an anti-oxidant/radical scavenger. The anti-oxidant/radical scavenger is especially useful for providing protection against UV radiation which can cause increased scaling or texture changes in the stratum corneum and against other environmental agents which can cause skin damage.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox$^R$), gallic acid and its alkyl esters, especially propyl gallate, uric acid and its salts and alkyl esters, sorbic acid and its salts, amines (e.g., N, N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, lysine, methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee, incorporated herein by reference.

(iv) Oroanic Hydroxy Acids: Compositions of the present invention may comprise an organic hydroxy acid. Suitable hydroxy acids include $C_1$–$C_{18}$ hydroxy acids, preferably $C_8$ or below. The hydroxy acids can be substituted or unsubstituted, straight chain, branched chain or cyclic (preferably straight chain), and saturated or unsaturated (mono- or poly- unsaturated) (preferably saturated). Non-limiting examples of suitable hydroxy acids include salicylic acid, glycolic acid, lactic acid, 5 octanoyl salicylic acid, hydroxyoctanoic acid, hydroxycaprylic acid, and lanolin fatty acids. Preferred concentrations of the organic hydroxy acid range from about 0. 1% to about 10%, more preferably from about 0.2% to about 5%, also preferably from about 0.5% to about 2%. Salicylic acid is preferred. The organic hydroxy acids enhance the skin appearance benefits of the present invention. For example, the organic hydroxy acids tend to improve the texture of the skin.

3. Water soluble skin conditioning component: Preferred compositions of the invention can also comprise a water soluble skin conditioning component comprising one or more water soluble skin conditioning compounds. The water soluble skin conditioning component is useful for lubricating the skin, increasing the smoothness and suppleness of the skin, preventing or relieving dryness of the skin, hydrating the skin, and/or protecting the skin. The skin conditioning component enhances the skin appearance improvements of the present invention, including but not limited to essentially immediate visual improvements in skin appearance. The water soluble skin conditioning component is preferably selected from the group consisting of humectants, moisturizers and mixtures thereof. The water soluble skin conditioning component is preferably present at a level of at least about 0.1%, more preferably from about 1% to about 99.99%, even more preferably from about 1% to about 50%, still more preferably from about 2% to about 30% and most preferably from about 5% to about 25% (e.g., about 5% to about 15%).

Nonlimiting examples of water soluble conditioning compounds include those selected from the group consisting of polyhydric alcohols, polypropylene glycols, dipropylene glycol, polyethylene glycols, ureas, pyrolidone carboxylic acids, ethoxylated and/or propoxylated C3–C6 diols and triols, alpha-hydroxy C2–C6 carboxylic acids, ethoxylated and/or propoxylated sugars, sugars having up to about 12 carbons atoms, sugar alcohols having up to about 12 carbon atoms, and mixtures thereof. Specific examples of useful water soluble conditioning agents include materials such as urea; guanidine; glycolic acid and glycolate salts (e.g. ammonium and quaternary alkyl ammonium); lactic acid and lactate salts (e.g. ammonium and quaternary alkyl ammonium); sucrose, fructose, glucose, eruthrose, erythritol, sorbitol, hydroxypropyl sorbitol, mannitol, glycerol, hexane triol, propylene glycol, butylene glycol, hexylene glycol, threitol, pentaerythritol, xylitol, glucitol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; and mixtures thereof. Also useful are materials such as aloe vera in any of its variety of forms (e.g., aloe vera gel); lactamide monoethanolamine; acetamide monoethanolamine; panthenol; and mixtures thereof. Also useful are ethoxylated glycerols and propoxylated glycerols as described in U.S. Pat. No. 4,976,953, to Orr et al., issued Dec. 11, 1990, which is incorporated by reference herein in its entirety.

4. Structuring Agent: The compositions hereof, and especially the emulsions hereof, may contain a structuring agent. Structuring agents are particularly preferred in the oil-in-water emulsions of the present invention. Without being limited by theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Preferred compositions of this invention comprise from about 1% to about 20%, more preferably from about 1% to about 10%, most preferably from about 2% to about 9%, of one or more structuring agents.

Preferred structuring agents are those having an HLB of from about 1 to about 8 and having a melting point of at least about 45° C. Suitable structuring agents are those selected from the group consisting of saturated $C_{14}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, $C_{14}$ to $C_{30}$ hydroxylated and nonhydroxylated saturated fatty acids, $C_{14}$ to $C_{30}$ saturated ethoxylated fatty acids, amines and alcohols containing from about 1 to about 5 moles of ethylene oxide diols, $C_{14}$ to $C_{30}$ saturated glyceryl mono esters with a monoglyceride content of at least 40%, $C_{14}$ to $C_{30}$ saturated polyglycerol esters having from about 1 to about 3 alkyl group and from about 2 to about 3 saturated glycerol units, $C_{14}$ to $C_{30}$ glyceryl mono ethers, $C_{14}$ to $C_{30}$ sorbitan mono/diesters, $C_{14}$ to $C_{30}$ saturated ethoxylated sorbitan mono/diesters with about 1 to about 5 moles of ethylene oxide, $C_{14}$ to $C_{30}$ saturated methyl glucoside esters, $C_{14}$ to $C_{30}$ saturated sucrose mono/diesters, $C_{14}$ to $C_{30}$ saturated ethoxylated methyl glucoside esters with about 1 to about 5 moles of ethylene oxide, $C_{14}$ to $C_{30}$ saturated polyglucosides having an average of between 1 to 2 glucose units and mixtures thereof, having a melting point of at least about 45° C.

The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from the group consisting of stearic acid, palmitic acid, stearyl alcohol, cetyl alcohol, behenyl alcohol, steareth-2, and mixtures thereof.

5. Anti-inflammatory Agents; A safe and effective amount of an anti-inflammatory agent may be added to the compositions of the subject invention, preferably from about 0.1% to about 10%, more preferably from about 0.5% to about 5%, of the composition. The anti-inflammatory agent enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, reference may be had to standard texts, including *Anti-inflammatory and Anti-Rheumatic Drugs*, K. D. Rainsford, Vol. I-III, CRC Press, Boca Raton, (1985), and *Anti-inflammatory Agents, Chemistry and Pharmacology*, 1, R. A. Scherrer, et al., Academic Press, New York (1974), each incorporated herein by reference.

Specific non-steroidal anti-inflammatory agents useful in the composition invention include, but are not limited to:
1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;

4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and
6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents. For example, etofenamate, a flufenamic acid derivative, is particularly useful for topical application. Of the nonsteroidal anti-inflammatory agents, ibuprofen, naproxen, flufenamic acid, etofenamate, aspirin, mefenamic acid, meclofenamic acid, piroxicam and felbinac are preferred; ibuprofen, naproxen, etofenamate, aspirin and flufenamic acid are most preferred.

Finally, so-called "natural" anti-inflammatory agents are useful in methods of the subject invention. Such agents may suitably be obtained as an extract by suitable physical and/or chemical isolation from natural sources (e.g., plants, fungi, by-products of microorganisms). For example, candelilla wax, alpha bisabolol, aloe vera, Manjistha (extracted from plants in the genus Rubia, particularly *Rubia Cordifolia*), and Guggal (extracted from plants in the genus Commiphora, particularly *Commiphora Mukul*), kola extract, chamomile, and sea whip extract, may be used.

Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$ –$C_{24}$ saturated or unsaturated esters of the acids, preferably $C_{10}$–$C_{24}$, more preferably $C_{16}$–$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

6. Sunscreens and Sunblocks: Exposure to ultraviolet light can result in excessive scaling and texture changes of the stratum corneum. Therefore, the compositions of the subject invention preferably contain a sunscreen or sunblock. Suitable sunscreens or sunblocks may be organic or inorganic.

A wide variety of conventional sunscreening agents are suitable for use herein. Sagarin, et al., at Chapter VIII, pages 189 et seq., of *Cosmetics Science and Technology* (1972), discloses numerous suitable agents, and is incorporated herein by reference. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-propyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylacetoumbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2', 4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one) and 4-isopropyl-di-benzoylmethane.

Of these, 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds, are preferred.

More preferred organic sunscreens useful in the compositions useful in the subject invention are 2-ethylhexyl-p-methoxycinnamate, butylmethoxydibenzoyl-methane, 2-hydroxy-4-methoxybenzo-phenone, 2-phenylbenzimidazole-5-sulfonic acid, octyldimethyl-p-aminobenzoic acid, octocrylene and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-arninobenzoic acid ester with 4-hydroxydibenzoylmethane; 4-N,N-(2-ethylhexyl)methyl-aminobenzoic acid ester of 2-hydroxy-4-(2-hydroxyethoxy) benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

Especially preferred sunscreens or sunblocks include butylmethoxydibenzoylmethane, 2-ethylhexyl-p-methoxycinnamate, phenyl benzimidazole sulfonic acid, and octocrylene.

A safe and effective amount of the sunscreen or sunblock is used, typically from about 1% to about 20%, more typically from about 2% to about 10%. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

7. Chelators: As used herein, "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995; all incorporated herein by reference. Preferred chelators useful in compositions of the subject invention are furildioxime and derivatives thereof.

8. Desquamation Agents/Exfoliants: A safe and effective amount of a desquamation agent may be added to the compositions of the subject invention, more preferably from about 0.1% to about 10%, even more preferably from about 0.2% to about 5%, also preferably from about 0.5% to about 4% of the composition. Desquamation agents enhance the skin appearance benefits of the present invention. For example, the desquamation agents tend to improve the texture of the skin (e.g., smoothness). A variety of desquamation agents are known in the art and are suitable for use herein, including but not limited to the organic hydroxy agents described above. One desquamation system that is suitable for use herein comprises sulfhydryl compounds and zwitterionic surfactants and is described in copending application Ser. No. 08/480,632, filed on Jun. 7, 1995 in the name of Donald L. Bissett, corresponding to PCT Application No. U.S. 95/08136, filed Jun. 29, 1995, each incorporated herein by reference. Another desquamation system that is suitable for use herein comprises salicylic acid and zwitterionic surfactants and is described in copending patent application Ser. No. 08/554,944, filed on Nov. 13, 1995 as a continuation of Ser. No. 08/209,401, filed on Mar. 9, 1994 in the name of Bissett, corresponding to PCI Application No. 94/12745, filed Nov. 4, 1994, published May 8, 1995, each incorporated herein by reference. Zwitterionic surfactants such as described in these applications are also useful as desquamatory agents herein, with cetyl betaine being particularly preferred.

9. Skin Lightening Agents: The compositions of the present invention may comprise a skin lightening agent. When used, the compositions preferably comprise from about 0.1% to about 10%, more preferably from about 0.2% to about 5%, also preferably from about 0.5% to about 2%, of a skin lightening agent. Suitable skin lightening agents include those known in the art, including kojic acid, arbutin, ascorbic acid and derivatives thereof, e.g., magnesium ascorbyl phosphate. Skin lightening agents suitable for use herein also include those described in copending patent application Ser. No. 08/479,935, filed on Jun. 7, 1995 in the name of Hillebrand, corresponding to PCT Application No. U.S. 95/07432, filed Jun. 12, 1995; and copending patent application Ser. No. 08/390,152, filed on Feb. 24, 1995 in the names of Kalla L. Kvalnes, Mitchell A. DeLong, Barton J. Bradbury, Curtis B. Motley, and John D. Carter, corresponding to PCT Application No. U.S. 95/02809, filed Mar. 1, 1995, published Sep. 8, 1995; all incorporated herein by reference.

D. Product Forms

As discussed hereinbefore in the section titled "Hydrophilic Liquid Carrier," the type of carrier utilized in the present invention depends on the type of product form desired for the composition. The product form, however, must utilize at least one hydrophilic liquid carrier or phase. Nonlimiting examples of product forms into which the compositions of the present invention can be formulated inlcude lotions and creams, cleansing compositions, and foundations. These product forms are further described as follows.

As noted, the topical compositions of the subject invention, including but not limited to lotions and creams, may comprise a dermatologically acceptable hydrophobic component. Such compositions in this product form preferably contain from about 1% to about 50% of the hydrophobic component. A wide variety of suitable hydrophobic components are known and may be used herein. Sagarin, *Cosmetics, Science and Technology*, 2nd Edition, Vol. 1, pp. 32–43 (1972), incorporated herein by reference, contains numerous examples of materials suitable as a hydrophobic component.

Lotions and creams according to the present invention generally comprise a solution carrier system and one or more hydrophobic components. Lotions typically comprise from about 1% to about 20%, preferably from about 2% to about 10%, of hydrophobic component; and from about 50% to about 90%, preferably from about 60% to about 80%, water. A cream typically comprises from about 2% to about 50%, preferably from about 3% to about 20%, of hydrophobic component; and from about 45% to about 85%, preferably from about 50% to about 75%, water.

Compositions of this invention useful for cleansing ("cleansers") are formulated with a suitable carrier, e.g., as described above, and preferably contain one or more dermatologically acceptable surfactants in an amount which is safe and effective for cleansing. Preferred compositions contain from about 1% to about 90%, more preferably from about 5% to about 10%, of a dermatologically acceptable surfactant. The surfactant is suitably selected from anionic, cationic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, sodium lauryl sulfate, and betaines such as described herein. See U.S. Pat. No. 4,800,197, to Kowcz et al., issued Jan. 24, 1989, which is incorporated herein by reference in its entirety, for exemplary surfactants useful herein. Examples of a broad variety of additional surfactants useful herein are described in *McCutcheon's Detergents and Emulsifiers*, North American Edition (1986), published by Allured Publishing Corporation, which is incorporated herein by reference in its entirety. The cleansing compositions can optionally contain, at their art-established levels, other materials which are conventionally used in cleansing compositions.

The physical form of the cleansing compositions is not critical. The compositions can be, for example, formulated as liquids, shampoos, bath gels, pastes, or mousses. Preferred rinse-off cleansing compositions, such as shampoos, include a delivery system adequate to deposit sufficient levels of actives on the skin and scalp. A preferred delivery system involves the use of insoluble complexes. For a more complete disclosure of such delivery systems, see U.S. Pat. No. 4,835,148, Barford et al., issued May 30, 1989, incorporated herein by reference in its entirety.

As used herein, the term "foundation" refers to a liquid, semi-liquid, or semi-solid skin cosmetic which includes, but is not limited to lotions, creams, gels, pastes, and the like. Typically the foundation is used over a large area of the skin, such as over the face, to provide a particular look. Foundations are typically used to provide an adherent base for color cosmetics such as rouge, blusher, and the like, and tend to hide skin imperfections and impart a smooth, even appearance to the skin. Foundations of the present invention include a dermatologically acceptable carrier for the essential particulate material and may include conventional ingredients such as oils, colorants, pigments, emollients, fragrances, waxes, stabilizers, and the like. Exemplary carriers and such other ingredients which are suitable for use herein are described, for example, in copending patent application Ser. No. 08/430,961, filed on Apr. 28, 1995 in the names of Marcia L. Canter, Brain D. Barford, and Brian D. Hofrichter, incorporated herein by reference.

V. Coverage Efficiency Ratio

The compositions of the present invention have a Coverage Efficiency Ratio of greater than about 20, preferably greater than about 25, more preferably greater than about 30, and most preferably greater than about 35. The Coverage Efficiency Ratio is calculated as follows:

$$\text{Coverage Efficiency Ratio} = \frac{\text{Coverage Index}}{\text{Weight \% of Reflective Particulate Material}}$$

For example, a composition containing 0.4% of charged $TiO_2$ and having a Coverage Index of 15 would deliver a Coverage Efficiency Ratio of 37.5.

The determination of coverage index involves measuring the transmission of light through a collagen film. Light transmission readings from a control collagen film (e.g., one without the product applied) is compared to light transmission readings from a collagen film on which product has been applied. The Coverage Index is then calculated as follows:

$$\text{Coverage Index} = \frac{\text{Control Mean} - \text{Test Product Mean}}{\text{Control Mean}} \times 100$$

The Coverage Index methodology requires a light source sufficiently powerful for sample illumination, a camera and video frame grabber for capturing the image of the sample on the collagen surface and a computer with video imaging software for data analysis and for viewing on a video monitor. Suitable image capture and analysis software includes Optimas 5.2 from Optimas Corp., Washington (refer to Image Analysis Software guide Volume I), the software and guide being incorporated herein by reference. Least significant differences can be performed on the data using Fischer's LSD method. A protocol describing the methods, procedures, and settings of the instruments for obtaining the Cover Index is provided in Examples 1–3.

VI. Preparation of Compositions

The compositions of the present invention can be generally prepared by conventional methods such as are known in the art of making topical compositions. Such methods typically involve mixing of the ingredients in one or more steps to a relatively uniform state, with or without heating, cooling, application of vacuum, and the like.

Typically one or more the components described hereinbefore can be mixed together with the charged particulate material via conventional methods in any sequence. The resulting mixture is then adjusted to the desired pH range from about 4 to about 8.5. Preferably, the components are first mixed together in any sequence. Then charged particulate material is added to the mixture after adjusting to the desired pH range from about 4 to about 8.5.

VII Methods for Regulating Skin Condition

The compositions of the present invention are useful for regulating mammalian skin condition (especially human skin, more especially human facial skin), including regulating visible and/or tactile discontinuities in skin, e.g., visible and/or tactile discontinuities in skin texture, more especially discontinuities associated with skin aging.

A wide range of quantities of the compositions of the present invention can be employed to provide a skin appearance and/or feel benefit. Quantities of the present compositions which are typically applied per application are, in mg composition/$cm^2$ skin, from about 0.1 mg/$cm^2$ to about 10 mg/$cm^2$. A particularly useful application amount is about 2 mg/$cm^2$. Typically applications would be on the order of about once per day, however application rates can vary from about once per week up to about three times per day or more.

The compositions of this invention provide a visible improvement in skin condition essentially immediately following application of the composition to the skin. Such immediate improvement involves coverage or masking of skin imperfections such as textural discontinuities (including those associated with skin aging, such as enlarged pores), and/or providing a more even skin tone or color.

In a preferred embodiment, the composition includes an active which chronically regulates skin condition and is topically applied chronically. "Chronic topical application" and the like involves continued topical application of the composition over an extended period during the subject's lifetime, preferably for a period of at least about one week, more preferably for a period of at least about one month, even more preferably for at least about three months, even more preferably for at least about six months, and more preferably still for at least about one year. Chronic regulation of skin condition involves improvement of skin condition following multiple topical applications of the composition to the skin. While benefits are obtainable after various maximum periods of use (e.g., five, ten or twenty years), it is preferred that chronic application continue throughout the subject's lifetime. Typically applications would be on the order of about once per day over such extended periods, however application rates can vary from about once per week up to about three times per day or more. Regulating skin condition involves topically applying to the skin a safe and effective amount of a composition of the present invention. The amount of the composition which is applied, the frequency of application and the period of use will vary widely depending upon the active levels of a given composition and the level of regulation desired, e.g., in light of the level of skin aging present in the subject and the rate of further skin aging.

Regulating skin condition is preferably practiced by applying a composition in the form of a skin lotion, cream, cosmetic, or the like which is intended to be left on the skin until skin cleansing is appropriate, for some esthetic, prophylactic, therapeutic or other benefit (i.e., a "leave-on" composition). After applying the composition to the skin, it is preferably left on the skin for a period of at least about 15 minutes, more preferably at least about 30 minutes, even more preferably at least about 1 hour, most preferably for at least several hours, e.g., up to about 12 hours.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are given in CTFA name.

Examples 1–3

Oil-in-water emulsions are prepared from the following ingredients using conventional formulating techniques.

|  |  | Comparative Example | Ex. 1 | Ex. 2 | Ex. 3 |
|---|---|---|---|---|---|
| Phase A: | Water | QS100 | QS100 | QS100 | QS100 |
|  | Disodium EDTA | 0.10 | 0.10 | 0.10 | 0.10 |
|  | Carbopol 1382 | 0.10 | 0.10 | 0.10 | 0.10 |
|  | Carbopol 954 | 0.50 | 0.50 | 0.50 | 0.50 |
|  | Sorbitan Monostearate/Sucrose Cocoate | 1.00 | 1.00 | 1.00 | 1.00 |
|  | Glycerin | 7.00 | — | — | — |
| Phase B: | Isopropyl Isostearate | 1.33 | 1.33 | 1.33 | 1.33 |
|  | Fatty acid ester of sugar[1] | 0.67 | 0.67 | 0.67 | 0.67 |
|  | Cetyl Ricinoleate | — | — | — | — |
|  | Isohexadecane | — | 4.00 | 4.00 | 4.00 |
|  | Silicone Treated $TiO_2$ (anatase) | 0.75 | — | — | — |
|  | Mica/$TiO_2$/$BaSO_4$[2] | — | — | 1.15 | — |
|  | Cetyl Alcohol | 0.72 | 0.72 | 0.72 | 0.72 |
|  | Stearyl Alcohol | 0.48 | 0.48 | 0.48 | 0.48 |
|  | PEG-100 Stearate | 0.10 | 0.10 | 0.10 | 0.10 |
|  | Stearic Acid | 0.10 | 0.10 | 0.10 | 0.10 |
|  | Vitamin E Acetate | — | 0.50 | 0.50 | — |
|  | Butylated Hydroxy Toluene | 0.001 | — | — | 0.001 |
| Phase C: | NaOH | 0.30 | 0.25 | 0.25 | 0.25 |
| Phase D: | Water | — | 5.00 | 5.00 | 5.00 |
|  | Kobo GLW75CA[3] | — | 0.534 | 0.400 | 0.534 |
|  | Glycerin | — | 6.93 | 6.93 | 6.93 |
| Phase E: | Water | 5.00 | 5.00 | 5.00 | 5.00 |
|  | Dexpanthenol | 0.50 | 0.50 | 0.50 | 0.50 |
|  | Niacinamide | 2.00 | 2.00 | 2.00 | 2.00 |
|  | Preservative | 0.10 | 0.10 | 0.10 | 0.10 |
|  | NaCl | 0.02 |  |  |  |
| Phase F: | Dimethicone (and) Dimethiconol | 2.00 | 2.00 | 2.00 | 2.00 |
| Phase G | Retinol | 0.05 | — | — | 0.05 |
|  | Vitamin E Acetate | 0.50 | — | — | 0.50 |

[1] A C1–C30 monoester or polyester of sugars and one or more carboxylic acid moieties as described herein, preferably a sucrose polyester in which the degree of esterification is 7–8, and in which the fatty acid moieties are C18 mono- and/or di-unsaturated and behenic, in a molar ratio of unsaturates:behenic of 1:7 to 3:5, more preferably the octaester of sucrose in which there are about 7behenic fatty acid moieties and about 1 oleic acid moiety in the molecule, e.g., sucrose ester of cottonseed oil fatty acids, e.g., SEFA Cottonate.
[2] Available as Naturaleaf ® powder from EM Idustries, Inc.
[3] A predispersion of ammonium polyacrylate treated $TiO_2$, water, glycerin, and ammonium zirconium carbonate.

For Examples 1 and 2: First, mix (using propeller type mixer) phase A ingredients in a suitable size vessel and heat to 70–75° C. In a separate vessel mix phase B ingredients and heat to 70–75° C. At 70–75° C., add phase B to phase A while continuing to mix. Then add phase C to the batch mixture of phases A/B while continuing to mix. The phase C component allows neutralization of the mixture. In a separate vessel, mix Phase D until uniform and then add to the batch mixture of phases A/B/C while continuing to mix. Cool to 50° C. Mix Phase E ingredients until uniform and then add to the batch mixture of phases A–D while continuing to mix. Then add Phase F ingredient to the batch mixture of A–E and continue to cool to about 35° C. Mixing is continued until the resulting batch mixture is uniform.

For the Comparative Example and Example 3: Follow the above for phases A–F. Then, when the batch mixture is cooled to about 35° C., mix the the phase G ingredients in a separate vessel and combined to the cooled batch mixture of phases A–F. Mixing is continued until the resulting batch mixture is uniform.

Applying each composition obtained from Examples 1–3 to a subject's facial skin at the rate of 2 mg composition/$cm^2$ skin to provides an essentially immediate visual improvement in skin appearance, e.g., reduced visibility of pores and a more even skin tone. Apply the composition to a subject's face at the same rate once or twice daily for a period of 3–6 months, to improve skin surface texture, including diminishing fine lines and wrinkles, in addition to the essentially immediate improvements in appearance.

Coverage Efficiency Ratio: The resulting compositions from Examples 1–3 should provide a Coverage Efficiency Ratio of greater than about 20. The Coverage Efficiency Ratio values for formulations Examples 1–3 and the Comparative Example are calculated below.

|  | Comparative Example | Ex. 1 | Ex. 2 | Ex. 3 |
|---|---|---|---|---|
| Coverage Index | 14.34 | 22.52 | 20.15 | 21.43 |
| TiO2 level (% of composition) | 0.75 | 0.40 | 0.45 | 0.40 |
| Coverage Efficiency Ratio | 19.1 | 56.3 | 44.8 | 53.6 |

The compositions obtained from Examples 1–3, containing the charged, refelective material, all provide a Coverage Efficiency of greater than about 20. In contrast, the composition obtained from the Comparative Example, which does not contain a charged, reflective material, provides a Coverage Efficiency of less than about 20.

The Coverage Index values of the compositions in Examples 1–3 are obtained by the following protocol: Using a collagen film having an exposed surface area of about 7 $cm^2$ (such as IMS #1192 or equivalent available from IMS Inc. Milford Conn.) mounted in a suitable holder, apply 40 microliters (using a Microman M50 pipette ) of product and spread evenly by hand on the film surface using 10 finger rotations. Optionally, the sample is mounted on a Zeiss SV-11 microscope (or equivalent) equipped with a 1X lens (the microscope is useful for enlarging the image which the camera is capturing; the effective magnification of this system is about 5 microns/pixel). A mounting template can optionally be employed to aid in repositioning the sample for multiple measurements. The SV-11 should be set up so that maximum light is being transmitted to the camera (e.g., a Sony 760-MD CCD 3 Camera). To insure proper positioning and a clear image, the equipment is set in the following manner. Camera controls are set so that the Gamma and Linear matrix switches are off. The camera control box settings are further defined as follows: Gain=0, White/Black balance on auto, iris- auto, mode-camera, detail-12 o'clock position, phase-0 degrees, SC-3 o'clock position, H-12 o'clock position, Color temp –3200 K, shutter off. The camera should be allowed to warm up for 15 minutes before adjusting white and black balance. Press the button labeled "white" to adjust the white balance, and adjust black balance by pulling the black adjustment rod and pushing the button that says black. Computer cables are connected to the RGB1 and Composite Sync.ports on the camera. The microscope Iris is set to completely open and a frosted glass plate is positioned in the microscope base for a uniformly lit field. A clear glass plate may optionally be used to adjust the sample height. Open the Optimas 5.2 program on the computer. Use a sample cup which is partially covered with black tape in the light path to adjust gain and offset (brightness). The reflecting mirror at the base of the microscope is set for maximum reflection into the microscope. The mean of the light source should be 245 to 254.5. The STD Deviation should be less than 3. If the mean is out of specifications check the light bulb alignment and mirror adjustment.

For the control, an untreated piece of collagen film (such as IMS #1192 available from IMS Inc. Milford Conn.), is mounted on a sample cup which is placed on the microscope such that the film lies in the center of the light path. The film is focused and light transmission through the film is measured using the image capture and analysis software. Multiple measurements are taken from separate areas of the sample, repositioning and refocusing the film for each measurement (seven or more measurements are taken). The histogram mean and standard deviation are determined using the image capture and analysis software.

For measuring light transmission by the test product, a piece of collagen film, having a surface area of about 7 $cm^2$, is first pre-hydrated with distilled water to insure flexibility. 40 microliters of test product is then dispensed on the film (e.g., using a Microman M50 pipette or equivalent), and spread evenly over its surface to produce an even film covering the surface of the collagen (generally by lightly spreading the material by applying 10 rotations of the finger, wearing a clean, latex finger cot, to the material). After waiting for a period of 5 minutes, the sample is mounted on the microscope base. Light transmission measurements through the film and product are then taken in the manner described for the control. Least significant differences can be performed on the data using Fischer's LSD method. The Coverage Index is calculated as follows:

$$\text{Coverage Index} = \frac{\text{Control Mean} - \text{Test Product mean}}{\text{Control Mean}} \times 100$$

*Control Mean: the mean light transmission reading for the untreated collagen film.

*Test Product Mean: the mean light transmission reading for for the treated collagen film.

Examples 4–7

Oil-in-water emulsions are prepared from the following ingredients using conventional formulating techniques.

|  |  | Ex. 4 | Ex. 5 | Ex. 6 | Ex. 7 |
|---|---|---|---|---|---|
| Phase A: | Water | QS100 | QS100 | QS100 | QS100 |
|  | Disodium EDTA | 0.10 | 0.10 | 0.10 | 0.10 |
|  | Carbopol 1382 | 0.10 | 0.10 | 0.10 | 0.10 |
|  | Carbopol 954 | 0.50 | 0.50 | 0.50 | 0.50 |
|  | Sorbitan Monostearate/ Sucrose Cocoate | 1.00 | 1.00 | — | 1.00 |
| Phase B: | Isopropyl Isostearate | 1.33 | 1.10 | 1.33 | 1.33 |
|  | Fatty acid ester of sugar[1] | 0.67 | — | 0.67 | 0.67 |
|  | Cetyl Ricinoleate | — | 1.25 | — | — |
|  | Isohexadecane | 4.00 | 2.00 | 4.00 | 4.00 |
|  | Caprylic/capric Triglycerides | — | 1.00 | — | — |
|  | Cetyl Alcohol | 0.72 | 0.72 | 0.72 | 0.72 |
|  | Stearyl Alcohol | 0.48 | 0.48 | 0.48 | 0.48 |
|  | PEG-100 Stearate | 0.10 | 0.10 | — | 0.10 |
|  | Stearic Acid | 0.10 | 0.10 | — | 0.10 |
|  | Vitamin E Acetate | 0.50 | 0.50 | — | — |
|  | Steareth-21 | — | — | 0.56 | — |
|  | Steareth-2 | — | — | 0.06 | — |
| Phase C: | NaOH | 0.25 | 0.25 | 0.25 | 0.25 |
| Phase D: | Water | 5.00 | 5.00 | 5.00 | 5.00 |
|  | Kobo GLW75CA[2] | 0.534 | 0.534 | 0.534 | — |
|  | Kobo BG60DC[3] | — | — | — | 0.534 |
|  | Glycerin | 6.93 | 6.93 | 6.93 | 6.93 |

-continued

|  |  | Ex. 4 | Ex. 5 | Ex. 6 | Ex. 7 |
|---|---|---|---|---|---|
| Phase E: | Water | 5.00 | 5.00 | 5.00 | 5.00 |
|  | Dexpanthenol | 0.50 | 0.50 | 0.50 | 0.50 |
|  | Niacinamide | 5.00 | 2.00 | 2.00 | 2.00 |
|  | Preservative | 0.10 | 0.10 | 0.10 | 0.10 |
| Phase F: | Dimethicone (and) Dimethiconol | 2.00 | 2.00 | 2.00 | 2.00 |

[1] A C1–C30 monoester or polyester of sugars and one or more carboxylic acid moieties as described herein, preferably a sucrose polyester in which the degree of esterification is 7–8, and in which the fatty acid moieties are C18 mono- and/or di-unsaturated and behenic, in a molar ratio of unsaturates:behenic of 1:7 to 3:5, more preferably the octaester of sucrose in which there are about 7 behenic fatty acid moieties and about 1 oleic acid moiety in the molecule, e.g., sucrose ester of cottonseed oil fatty acids, e.g., SEFA Cottonate.
[2] A predispersion of ammonium polyacrylate treated $TiO_2$, water, glycerin, and ammonium zirconium carbonate.
[3] A predispersion of chitosan treated $TiO_2$ and butylene glycol.

The compositions in Examples 4–7 are prepared in the manner described for Examples 1–3. Apply each composition obtained from Examples 5–7 to a subject's facial skin at the rate of 2 mg composition/cm² skin to provide an essentially immediate visual improvement in skin appearance, e.g., reduced visibility of pores and a more even skin tone. Apply the composition to a subject's face at the same rate once or twice daily for a period of 3–6 months, to improve skin surface texture, including diminishing fine lines and wrinkles, in addition to the essentially immediate improvements in appearance.

Example 8–9

Oil-in-water emulsions are prepared from the following ingredients using conventional formulating techniques.

|  |  | Ex. 8 | Ex. 9 |
|---|---|---|---|
| Phase A: | Water | QS100 | QS100 |
|  | Disodium EDTA | 0.10 | 0.10 |
|  | Sorbitan Monostearate/Sucrose Cocoate | 1.00 | 1.00 |
| Phase B: | Isopropyl Isostearate | 1.33 | 1.33 |
|  | Fatty acid ester of sugar[1] | 0.67 | 0.67 |
|  | Isohexadecane | 3.00 | 3.00 |
|  | Cetyl Alcohol | 0.72 | 0.72 |
|  | Stearyl Alcohol | 0.48 | 0.48 |
|  | PEG-100 Stearate | 0.10 | 0.10 |
|  | Stearic Acid | 0.10 | 0.10 |
| Phase C: | NaOH | 0.013 | 0.013 |
| Phase D: | Water | 5.00 | 5.00 |
|  | Kobo GLW75CA[2] | 0.543 | 0.543 |
|  | Glycerin | 6.93 | 6.93 |
| Phase E: | Sepigel 305[3] | 2.50 | 2.50 |
| Phase F: | Water | 5.00 | 5.00 |
|  | Dexpanthenol | 0.50 | 0.50 |
|  | Niacinamide | 2.00 | 5.00 |
|  | Preservative | 0.10 | 0.10 |
| Phase G: | Dimethicone (and) Dimethiconol | 2.00 | 2.00 |

A C1–C30 monoester or polyester of sugars and one or more carboxylic acid moieties as described herein, preferably a sucrose polyester in which the degree of esterification is 7–8, and in which the fatty acid moieties are C18 mono- and/or di-unsaturated and behenic, in a molar ratio of unsaturates:behenic of 1:7 to 3:5, more preferably the octaester of sucrose in which there are about 7 behenic fatty acid moieties and about 1 oleic acid moiety in the molecule, e.g., sucrose ester ofcottonseed oil fatty acids, e.g., SEFA Cottonate.
[2] A predispersion of ammonium polyacrylate treated $TiO_2$, water, glycerin, and ammonium zirconium carbonate.
[3] A mixture of polyacrylamide, isoparaffin, laureth-7

First, mix (using propeller type mixer) phase A ingredients in a suitable sized vessel and heat to 70–75° C. In a separate vessel mix phase B ingredients and heat to 70–75° C. At 70–75° C. phase B to phase A while continuing to mix. Then add phase C. In a separate vessel, mix phase D until uniform and then add phase D to the batch mixture of phases A/B/C while continuing to mix. Cool the batch mixture of phases A–D to 60° C. while continuing to mix. Then add phase E and cool the batch mixture of phases A–E to 50° C. In a separate vessel, mix Phase F ingredients until uniform, and then add to the batch mixture of phases A-E while continuing to mix. Then add the Phase G ingredient to the batch and continue to cool to 35° C.

The resulting compositions from Examples 8 and 9 have a Coverage Efficiency Raio of 46.5 and 47.6, respectively. The Coverage Index is obtained by following the protocol outlined in Examples 1–3.

|  | Ex. 8 | Ex. 9 |
|---|---|---|
| Coverage Index | 18.56 | 19.02 |
| TiO2 level (% of composition) | 0.40 | 0.40 |
| Coverage Efficiency Ratio | 46.5 | 47.6 |

Application to the skin of the compositions obtained from Examples 8 and 9 to a subject's facial skin at the rate of 2 mg composition/cm² skin provides an essentially immediate visual improvement in skin appearance, e.g., reduced visibility of pores and a more even skin tone. Apply the composition to a subject's face at the same rate once or twice daily for a period of 3–6 months, to improve skin surface texture, including diminishing fine lines and wrinkles, in addition to the essentially immediate improvements in appearance.

Example 10

A thickened gel is prepared from the following ingredients using conventional formulating techniques.

|  |  | Ex. 10 |
|---|---|---|
| Phase A: | Water | QS 100 |
|  | Disodium EDTA | 0.10 |
|  | Carbopol 1382 | 0.10 |
|  | Carbopol 954 | 0.50 |
| Phase B: | NaOH | 0.25 |
| Phase C: | Water | 5.00 |
|  | Kobo GLW75CA [1] | 0.543 |
|  | Glycerin | 6.93 |
| Phase D: | Water | 5.00 |
|  | Dexpanthenol | 0.50 |
|  | Niacinamide | 5.00 |
|  | Preservative | 0.10 |

[1] A predispersion of ammonium polyacrylate treated $TiO_2$, water, glycerin, and ammonium zirconium carbonate.

In a suitable size vessel, mix (using propeller type) phase A ingredients and heat to 70–75° C. At 70–75° C., add phase B to phase A while continuing to mix. In a separate vessel, mix Phase C until uniform and then add phase C to the batch mixture of phases A/B while continuing to mix. Cool to 50° C. In a separate vessel, mix Phase D ingredients until uniform and then add to the batch mixture of phases A–C while continuing to mix. Then cool to 35C.

Apply the composition obtained from Example 10 to a subject's facial skin at the rate of 2 mg composition/cm² skin to provide an essentially immediate visual improvement in skin appearance, e.g., reduced visibility of pores and a more even skin tone. Apply the composition to a subject's face at the same rate once or twice daily for a period of 3-6 months, to improve skin surface texture, including diminishing fine lines and wrinkles, in addition to the essentially immediate improvements in appearance.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope ofthe subject invention.

What is claimed is:

1. A skin care composition which upon topical application to skin provides immediate visual improvement of skin appearance, which composition is in the form of an oil-in-water or water-in-oil emulsion, and which composition comprises:

(A) a hydrophilic phase comprising:
  (i) from about 1% to about 98.98%, by weight of the composition, of a hydrophilic liquid carrier;
  (ii) from about 0.01% to about 10%, by weight of the composition, of a polymeric thickening agent for said hydrophilic liquid carrier, wherein said polymeric thickening agent is selected from the soup consisting of carboxylic acid polymers, crosslinked polyacrylate polymers, polyacrylamide polymers, acrylates/C10–C30 alkyl acrylate crosspolymers, crosslinked alkyl vinyl ethers and maleic anhydride copolymers, crosslinked poly(N-vinylpyrrolidones), polysaccharides, and mixtures thereof; and
  (iii) from about 0.01% to about 2%, by weight of the composition, of a charged reflective particulate material having an average, primary, neat particle size from about 100 nm to about 300 nm, said charged particulate material being dispersed throughout said thickened hydrophilic liquid carrier, which charged reflective particulate material comprises:
    a) a metal oxide material, wherein said metallic oxide is selected from the group consisting of $TiO_2$, ZnO, $ZrO_2$, and combinations thereof; and
    b) a coating material for said metal oxide material, which coating material imparts a net anionic or cationic charge to said metal oxide material which is greater than the net charge of the uncoated metal oxide material, and wherein said coating material is selected from the group consisting of chitosan, hydroxypropyl chitosan, quaternium-80, polyquaternium-7, ammonium polyacrylate, sodium polyacrylate, potassium polyacrylate, ethylene acrylic acid copolymer, hydrolyzed wheat protein polysiloxane copolymer, dimethicone copolyol phosphate, dimethicone copolyol acetate, dimethicone copolyol laurate, dimethicone copolyol stearate, dimethicone copolyol behenate, dimethicone copolyol isostearate, dimethicone copolyol hydroxystearate, phosphate ester, sodium chondroiton sulfate, sodium hyaluronate, ammonium hyaluronate, sodium algenate, ammonium algenate, ammonium laurate, sodium laurate, potassium laurate, ammonium myristate, sodium myristate, potassium myristate, ammonium palmitate, sodium palmitate, potassium palmitate, ammonium stearate, sodium stearate, potassium stearate, ammonium oleate, sodium oleate, potassium oleate, and mixtures thereof; and (B) from about 1% to about 98%, by weight of the composition, of a hydrophobic phase.

2. A method of manufacturing a topical, aesthetically pleasing composition for providing skin conditioning and immediate visual improvement of skin appearance, comprising the steps of (A) mixing together, in any sequence,
  (1) from about 1% to about 98%, by weight of the composition, of a hydrophilic carrier;
  (2) from about 0.01% to about 20%, by weight of the composition, of a polymeric thickening agent for said hydrophilic carrier, wherein said polymeric thickening agent is selected from the group consisting of carboxylic acid polymers, crosslinked polyacrylate polymers, polyacrylamide polymers, acrylates/C10–C30 alkyl acrylate crosspolymers, crosslinked alkyl vinyl ethers and maleic anhydride copolymers, crosslinked poly(N-vinylpyrrolidones), polysaccharides, and mixtures thereof;
  (3) from about 1% to about 98%, by weight of the composition, of a hydrophobic phase; and
  (4) from about 0.01% to about 2%, by weight of the composition, of a charged particulate material having an average, primary, neat particle size from about 100 nm to about 300 nm, said charged particulate material being dispersed throughout said thickened hydrophilic phase, wherein said charged particulate material comprises:
    a) a metal oxide material, wherein said metallic oxide is selected from the group consisting of $TiO_2$, ZnO, $ZrO_2$, and combination thereof; and
    b) a coating material for said metal oxide material, which coating material imparts a net anionic or cationic charge to said metal oxide material which is greater than the net charge of the uncoated metal oxide material, and wherein said coating material is selected from the group consisting of chitosan, hydroxypropyl chitosan, quaternium-80, polyquaternium-7, ammonium polyacrylate sodium polyacrylate, potassium polyacrylate, ethylene acrylic acid copolymer, hydrolyzed wheat protein polysiloxane copolymer, dimethicone copolyol phosphate, dimethicone copolyol acetate, dimethicone copolyol laurate, dimethicone copolyol stearate, dimethicone copolyol behenate, dimethicone copolyol isostearate, dimethicone copolyol hydroxystearate, phosphate ester, sodium chondroiton sulfate, sodium hyaluronate, ammonium hyaluronate, sodium algenate, ammonium algenate, ammonium laurate, sodium laurate, potassium laurate, ammonium myristate, sodium myristate, potassium myristate, ammonium palmitate, sodium palmitate, potassium palmitate, ammonium stearate, sodium stearate, potassium stearate, ammonium oleate, sodium oleate, potassium oleate, and mixtures thereof; and (B) adjusting the pH of the mixture of (A) to a pH from about 4 to about 8.5, wherein said composition provides a Coverage Efficiency Ratio of greater than about 20.

3. The composition of claim 1 wherein said composition comprises from about 0.05% to about 1.5% of said charged reflective particulate material, from about 0.1% to about 5% of said polymeric thickening agent, and wherein said Coverage Efficiency Ratio is greater than about 25.

4. The composition according to claim 1 wherein said metallic oxide consists essentially of $TiO_2$.

5. The composition according to claim 1 wherein said coating material is selected from the group consisting of ammonium polyacrylate, sodium polyacrylate, and mixtures thereof.

6. The composition according to claim 1 wherein said polymeric thickening agent is selected from the group consisting of carboxylic acid polymers, polyacrylamide polymers, acrylates/C10–$C_{30}$ alkyl acrylate crosspolymers, and mixtures thereof.

7. The composition according to claim 1 wherein the composition comprises a continuous hydrophilic phase and a hydrophobic phase dispersed in the hydrophilic phase.

8. The composition according to claim 1 wherein the composition comprises a continuous hydrophobic phase and a hydrophilic phase dispersed in the hydrophobic phase.

9. The composition according to claim 1 wherein the composition further comprises one or more compounds selected from the group consisting of emulsifiers, surfactants, structuring agents, skin care actives, and combinations thereof.

10. The composition according to claim 9 wherein
(A) said emulsifier or surfactant is selected from the group consisting of hydrophilic, non-ionic emulsifiers and surfactants having an HLB of at least about 8;
(B) said structuring agent has an HLB of from about 1 to about 8 and a melting point of at least about 45° C.; and
(C) said skin care active is selected from the group consisting of vitamin $B_3$ compounds, retinoids, antioxidants, and mixtures thereof.

11. The composition according to claim 10 comprising from about 0.05% to about 5% of the emulsifier or surfactant; from about 1% to about 20% of the structuring agent; and from about 0.0001% to about 20% of the skin care active.

12. The composition according to claim 10 wherein the nonionic surfactant comprises a compound selected from the group consisting of steareth-21, ceteareth-20, ceteareth-12, sucrose cocoate, steareth-100, PEG-100 stearate, and mixtures thereof.

13. The composition according to claim 10 wherein the structuring agent is selected from the group consisting of saturated $C_{14}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, $C_{14}$ to $C_{30}$ hydroxylated and nonhydroxylated saturated fatty acids, C14 to $C_{30}$ saturated ethoxylated fatty acids, amines and alcohols containing from about 1 to about 5 moles of ethylene oxide diols, $C_{14}$ to $C_{30}$ saturated glyceryl mono esters with a monoglyceride content of at least 40%, $C_{14}$ to $C_{30}$ saturated polyglycerol esters having from about 1 to about 3 alkyl group and from about 2 to about 3 saturated glycerol units, $C_{14}$ to $C_{30}$ glyceryl mono ethers, $C_{14}$ to $C_{30}$ sorbitan mono/diesters, $C_{14}$ to $C_{30}$ saturated ethoxylated sorbitan mono/diesters with about 1 to about 5 moles of ethylene oxide, $C_{14}$ to $C_{30}$ saturated methyl glucoside esters, $C_{14}$ to $C_{30}$ saturated sucrose monodiesters, $C_{14}$ to $C_{30}$ saturated ethoxylated methyl glucoside esters with about 1 to about 5 moles of ethylene oxide, $C_{14}$ to $C_{30}$ saturated polyglucosides having an average of between 1 to 2 glucose units and mixtures thereof.

14. A composition according to claim 10 wherein said one or more skin care active is selected from the group consisting of niacinamide, retinol, retinal, retinyl palmitate, retinyl propionate, ascorbic acid, tocopherol, and derivatives and mixtures thereof.

15. The composition according to claim 1 wherein the composition has an apparent viscosity, in centipoise, of from about 5,000 to about 200,000, and wherein said composition has a final pH of about 4 to about 8.5.

16. The composition according to claim 1 further comprising a transparent particulate material selected from the group consisting of mica, mica treated with barium sulfate and $TiO_2$, silica, nylon, polyethylene, talc, styrene, polypropylene, ethylene/acrylic acid copolymer, sericite, aluminum oxide, silicone resin, barium sulfate, calcium carbonate, cellulose acetate, polymethyl methacrylate, and mixtures thereof.

17. A method of regulating skin condition comprising topically applying the composition of claim 1.

18. The method according to claim 17 wherein regulating skin condition comprises masking imperfections on the skin surface.

* * * * *

UNITED STATES PATENT AND TRADEMARK OFFICE
CERTIFICATE OF CORRECTION

PATENT NO.     : 5,997,887
DATED          : December 7, 1999
INVENTOR(S)    : Robert Bao Kim Ha et al.

It is certified that error appears in the above-identified patent and that said Letters Patent is hereby corrected as shown below:

At column 1, line 43 "Vol. III" should read --Vol. 111--.

At column 8, line 1 "(A)$hd\ l$, (B)$_m$, and (C)$_n$" should read --(A)$_l$, (B)$_m$, and (C)$_n$--.

At column 11, line 43 "Stabilezer" should read --Stabileze--.

At column 15, line 63 "e.,g.," should read --e.g.,--

At column 17, line 15 "Dow Coming" should read --Dow Corning--.

At column 17, line 21 "where" should read --wherein R is--.

At column 17, line 30 "[SiR$_2$-O]n" should read --[SiR$_2$-O]$_n$--.

At column 17, line 44 "Dow Coming" should read --Dow Corning--.

At column 18, line 46 "discontinues" should read --discontinuous--.

At column 19, line 13 "discontinues" should read --discontinuous--.

At column 20, line 45 "thereof Z preferably" should read --thereof. Z preferably--.

At column 20, line 50 "R$^2$ CO- moicty" should read --R$^2$CO- moiety--.

At column 21, line 19 "fany acid" should read --fatty acid--

At column 21, line 30 "*Deteroents*" should read --*Detergents*--.

At column 21, line 48 "Interscience" should read --Interscience--.

At column 22, line 39 "-(CH$_2$)n-O-(CH$_2$CHR$^3$O)m-H" should read -- -(CH$_2$)$_n$-O-(CH$_2$CHR$^3$O)$_m$-H --.

At column 22, line 40 "-(CH$_2$)n-O-(CH$_2$CHR$^3$O)m-(CH$_2$CHR$^4$O)o-H" should read -- -(CH$_2$)$_n$-O-(CH$_2$CHR$^3$O)$_m$-(CH$_2$CHR$^4$O)$_o$-H --.

At column 22, line 42 "consisting of 11" should read --consisting of H--.

UNITED STATES PATENT AND TRADEMARK OFFICE
CERTIFICATE OF CORRECTION

PATENT NO. : 5,997,887

DATED : December 7, 1999

INVENTOR(S) : Robert Bao Kim Ha et al.

It is certified that error appears in the above-identified patent and that said Letters Patent is hereby corrected as shown below:

At column 23, line 30 "*Inttredient*" should read --*Ingredient*--.

At column 23, line 60 "*Cosmeticoloy*" should read --*Cosmeticology*--.

At column 24, line 55 "B, compound" should read --$B_3$ compound--.

At column 25, line 7 "$C1_{-C_{16}}$" should read --$C_1$–$C_{16}$--

At column 25, line 51 "olycolic acid" should read --glycolic acid--.

At column 26, line 16 "D-Iosascorbic" should read --D-Iosascorbic--.

At column 28, line 20 "Oroanic" should read --Organic--.

At column 32, line 55 "arninobenzoic" should read --aminobenzoic--.

At column 33, line 56 "PCI Application" should read --PCT Application--.

At column 33, line 57 "May 8, 1995" should read --May 18, 1995--.

At column 35, line 49 "Coveragc" should read --Coverage--.

At column 40, lines 35-36 "reading for for the" should read --reading for the--.

At column 41, line 56 "A C1-C30" should read --$^1$A C1-C30--

At column 41, lines 59-60 "bebenic" should read --behenic--.

At column 41, line 60 "prefcrably" should read --preferably--.

At column 42, line 2 "C. phase B" should read --C., add phase B --.

At column 43, line 12 "ofthe" should read --of the--.

At column 43, line 24 "soup" should read --group--.

At column 43, line 60 "alegenate" should read --algenate--.

UNITED STATES PATENT AND TRADEMARK OFFICE
CERTIFICATE OF CORRECTION

PATENT NO.    :    5,997,887
DATED         :    December 7, 1999
INVENTOR(S)   :    Robert Bao Kim Ha et al.

It is certified that error appears in the above-identified patent and that said Letters Patent is hereby corrected as shown below:

At column 44, line 30 "combination thereof" should read --combinations thereof--.
At column 44, lines 38-39 "polyacrylate sodium" should read --polyacrylate, sodium--.
At column 46, line 15 "monodiesters" should read --mono/diesters--.

Signed and Sealed this

Twenty-second Day of May, 2001

Attest:

NICHOLAS P. GODICI

Attesting Officer    Acting Director of the United States Patent and Trademark Office